US008226957B2

(12) United States Patent
Van Nest

(10) Patent No.: US 8,226,957 B2
(45) Date of Patent: Jul. 24, 2012

(54) METHODS OF PREVENTING AND TREATING RESPIRATORY VIRAL INFECTION USING IMMUNOMODULATORY POLYNUCLEOTIDE SEQUENCES

(75) Inventor: Gary Van Nest, Martinez, CA (US)

(73) Assignee: Dynavax Technologies Corporation, Berkeley, CA (US)

( * ) Notice: Subject to any disclaimer, the term of this patent is extended or adjusted under 35 U.S.C. 154(b) by 222 days.

(21) Appl. No.: 12/510,849

(22) Filed: Jul. 28, 2009

(65) Prior Publication Data

US 2010/0035975 A1 Feb. 11, 2010

Related U.S. Application Data

(63) Continuation of application No. 09/802,686, filed on Mar. 9, 2001, now abandoned.

(60) Provisional application No. 60/188,583, filed on Mar. 10, 2000.

(51) Int. Cl.
*C12P 19/34* (2006.01)
*A61K 39/155* (2006.01)
*C07H 21/02* (2006.01)

(52) U.S. Cl. ............ 424/211.1; 424/278.1; 536/23.1; 514/44 R

(58) Field of Classification Search .............. None
See application file for complete search history.

(56) References Cited

U.S. PATENT DOCUMENTS

| 4,458,066 A | 7/1984 | Caruthers et al. |
| 4,650,675 A | 3/1987 | Borel et al. |
| 4,849,513 A | 7/1989 | Smith et al. |
| 4,910,300 A | 3/1990 | Urdea et al. |
| 4,948,882 A | 8/1990 | Ruth |
| 5,015,733 A | 5/1991 | Smith et al. |
| 5,093,232 A | 3/1992 | Urdea et al. |
| 5,118,800 A | 6/1992 | Smith et al. |
| 5,118,802 A | 6/1992 | Smith et al. |
| 5,124,246 A | 6/1992 | Urdea et al. |
| 5,453,496 A | 9/1995 | Caruthers et al. |
| 5,616,461 A | 4/1997 | Schaffer et al. |
| 5,663,153 A | 9/1997 | Hutcherson et al. |
| 5,723,335 A | 3/1998 | Hutcherson et al. |
| 5,849,719 A | 12/1998 | Carson et al. |
| 5,874,089 A | 2/1999 | Schlegel et al. |
| 6,174,872 B1 | 1/2001 | Carson et al. |
| 6,218,371 B1 | 4/2001 | Krieg et al. |
| 6,239,116 B1 | 5/2001 | Krieg et al. |
| 6,339,068 B1 | 1/2002 | Krieg |
| 6,406,705 B1 | 6/2002 | Davis et al. |
| 6,498,148 B1 * | 12/2002 | Raz .......................... 514/44 R |
| 6,514,948 B1 | 2/2003 | Raz et al. |
| 6,534,062 B2 | 3/2003 | Raz et al. |
| 6,552,006 B2 | 4/2003 | Raz et al. |
| 6,613,751 B2 | 9/2003 | Raz et al. |
| 7,157,437 B2 | 1/2007 | Van Nest |
| 7,713,529 B2 | 5/2010 | Krieg et al. |

| 2001/0046967 A1 | 11/2001 | Van Nest |
| 2002/0028784 A1 | 3/2002 | Nest |
| 2002/0098199 A1 | 7/2002 | Van Nest et al. |
| 2002/0107212 A1 | 8/2002 | Nest et al. |
| 2003/0050263 A1 | 3/2003 | Krieg et al. |
| 2003/0092663 A1 | 5/2003 | Raz |
| 2003/0216340 A1 | 11/2003 | Van Nest et al. |
| 2004/0009942 A1 | 1/2004 | Van Nest |
| 2004/0030118 A1 * | 2/2004 | Wagner et al. ............. 536/23.72 |
| 2005/0059626 A1 | 3/2005 | Van Nest et al. |
| 2005/0101554 A1 | 5/2005 | Krieg et al. |
| 2007/0060540 A1 | 3/2007 | Van Nest |

FOREIGN PATENT DOCUMENTS

| EP | 0 468 520 A2 | 1/1992 |
| EP | 0 468 520 A3 | 1/1992 |
| WO | WO-96/02555 A1 | 2/1996 |
| WO | WO-97/28259 A1 | 8/1997 |
| WO | WO-98/16247 A1 | 4/1998 |
| WO | WO-98/18810 A1 | 5/1998 |
| WO | WO-98/37919 A1 | 9/1998 |
| WO | WO-98/40100 A1 | 9/1998 |
| WO | WO-98/52581 A1 | 11/1998 |
| WO | WO-98/52581 C2 | 11/1998 |
| WO | WO-98/52962 A1 | 11/1998 |
| WO | WO-98/55495 A2 | 12/1998 |
| WO | WO-98/55495 A3 | 12/1998 |
| WO | WO-98/55495 B1 | 12/1998 |
| WO | WO-98/55609 A1 | 12/1998 |
| WO | WO-99/11275 A2 | 3/1999 |
| WO | WO-99/11275 A3 | 3/1999 |
| WO | WO-99/11275 C2 | 3/1999 |

(Continued)

OTHER PUBLICATIONS

Agrawal, S. et al. (2002). "Medicinal Chemistry and Therapeutic Potential of CpG DNA," *Trends in Molecular Medicine* 8(3):114-121.
Agrawal, S. et al. (2003). "Was Induction of HIV-1 Through TLR9?" *J. Immunol.* 171:1621-1622.
Aoki, N. et al. (2004). "Use of Cytokines in Infection," *Expert Opin. Emerg. Drugs* 9(2):223-236.
Ausubel, F.M. et al., eds. (1995). *Current Protocols in Molecular Biology*. vol. 1, John Wiley & Sons, Inc.: pp. iii-xii (Table of Contents).
Ballas, Z. et al. (1996). "Induction of NK Activity in Murine and Human Cells by CpG Motifs in Oligodeoxynucleotides and Bacterial DNA" *J. Immunol.* 157:1840-1845.

(Continued)

*Primary Examiner* — Nita M Minnifield
*Assistant Examiner* — Nina Archie
(74) *Attorney, Agent, or Firm* — Morrison & Foerster LLP

(57) ABSTRACT

The invention provides methods of preventing and/or treating infection by a respiratory virus such as respiratory syncytial virus (RSV), particularly reducing infection and/or one or more symptoms of respiratory virus infection. A polynucleotide comprising an immunostimulatory sequence (an "ISS") is administered to an individual which is at risk of being exposed to a respiratory virus, has been exposed to a respiratory virus or is infected with a respiratory virus. The ISS is administered without any antigens of the respiratory virus. Administration of the ISS results in reduced incidence and/or severity of one or more symptoms of respiratory virus infection.

7 Claims, 1 Drawing Sheet

FOREIGN PATENT DOCUMENTS

| | | |
|---|---|---|
| WO | WO-99/33488 A2 | 7/1999 |
| WO | WO-99/33488 A3 | 7/1999 |
| WO | WO-99/33868 A2 | 7/1999 |
| WO | WO-99/33868 A3 | 7/1999 |
| WO | WO-99/51259 A2 | 10/1999 |
| WO | WO-99/51259 A3 | 10/1999 |
| WO | WO-99/56755 A1 | 11/1999 |
| WO | WO-99/62923 A2 | 12/1999 |
| WO | WO-99/62923 A3 | 12/1999 |
| WO | WO-00/06588 A1 | 2/2000 |
| WO | WO-00/06588 B1 | 2/2000 |
| WO | WO-00/16804 A1 | 3/2000 |
| WO | WO-00/21556 A1 | 4/2000 |
| WO | WO-00/21556 C2 | 4/2000 |
| WO | WO-00/62802 A2 | 10/2000 |
| WO | WO-00/62802 A3 | 10/2000 |
| WO | WO-00/67023 A1 | 11/2000 |
| WO | WO-01/02007 A1 | 1/2001 |
| WO | WO-01/12223 A2 | 2/2001 |
| WO | WO-01/12223 A3 | 2/2001 |
| WO | WO-01/55341 A2 | 8/2001 |
| WO | WO-01/55341 A3 | 8/2001 |
| WO | WO-01/68077 A2 | 9/2001 |
| WO | WO-01/68077 A3 | 9/2001 |
| WO | WO-01/68078 A2 | 9/2001 |
| WO | WO-01/68078 A3 | 9/2001 |
| WO | WO-01/68103 A2 | 9/2001 |
| WO | WO-01/68103 A3 | 9/2001 |
| WO | WO-01/68103 C2 | 9/2001 |
| WO | WO-01/68116 A2 | 9/2001 |
| WO | WO-01/68116 A3 | 9/2001 |
| WO | WO-01/68117 A2 | 9/2001 |
| WO | WO-01/68117 A3 | 9/2001 |
| WO | WO-01/68143 A2 | 9/2001 |
| WO | WO-01/68143 A3 | 9/2001 |
| WO | WO-01/68144 A2 | 9/2001 |
| WO | WO-01/68144 A3 | 9/2001 |
| WO | WO-01/76642 A1 | 10/2001 |

OTHER PUBLICATIONS

Baumann, N.M. et al. (Dec. 1996). "Recurrent Respiratory Papillomatosis," *Pediatric Otolarynology* 43(6):1385-1401.

Beaucage, S.L. (1993). "Oligodeoxyribonucleotide Synthesis" vol. 20 Chapter 3 in *Protocols for Oligonucleotides and Analogs, Synthesis and Properties*, Agrawal (ed.), Humana Press: Totowa, NJ. pp. 33-61.

Beutner, K.R. et al. (Feb. 1998). "Treatment of Genital Warts with an Immune-respnse Modifier (Imiquimod)," *Journal of the American Academy of Dermatology* 38(2, part 1):230-239.

Bohn, E. et al. (May 1998). "Ambiguous Role of Interleukin-12 in *Yersinia enterocolitica* Infection in Susceptible and Resistant Mouse Strains," *Infect. Immun.* 66(5):2213-2220.

Branda, R.F. et al. (1993). "Immune Stimulation by an Antisense Oligomer Complementary to the Rev Gene of HIV-1" *Biochem. Pharmacol.* 45(10):2037-2043.

Branda, R.F. et al. (1996). "Amplification of Antibody Production by Phosphorothioate Oligodeoxynucleotides" *J. Lab. Clin. Med.* 128(3):329-338.

Braun, R.P. et al. (1988). "Immunogenic Duplex Nucleic Acids are Nuclease Resistant" *J. Immunol.* 141(6):2084-2089.

Brazolot Millan, C.L. et al. (1998). "CpG DNA can Induce Strong Th1 Humoral and Cell-Mediated Immune Responses Against Hepatitis B Surface Antigen in Young Mice" *Proc. Natl. Acad. Sci. USA* 95:15553-15558.

Broide, D. et al. (1999). "DNA-Based Immunization for Asthma" *Int. Arch. Allergy Immunol.* 118:453-456.

Broide, D. et al. (1998). "Immunostimulatory DNA Sequences Inhibit IL-5, Eosinophilic Inflammation, and Airway Hyperresponsiveness in Mice" *J. Immunol.* 161:7054-7062.

Carson, D.A. et al. (1997). "Oligonucleotide Adjuvants for T Helper 1 (Th1)-Specific Vaccination" *J. Exp. Med.* 186(10):1621-1622.

Chace, J.H. et al. (1997). "Bacterial DNA-Induced NK Cell IFN-Gamma Production is Dependent on Macrophage Secretion of IL-12" *Clin. Immunol. and Immunopathol.* 84(2):185-193.

Chaturvedi, S. et al. (1996). "Stabilization of Triple-Stranded Oligonucleotide Complexes: Use of Probes Containing Alternating Phosphodiester and Stereo-Uniform Cationic Phosphoramidate Linkages" *Nucleic Acids Res.* 24(12):2318-2323.

Chu, R.S. et al. (1997). "CpG Oligodeoxynucleotides Act as Adjuvants that Switch on T Helper 1 (Th1) Immunity" *J. Exp. Med.* 186(10):1623-1631.

Cianci, C. et al. (Jul. 2004). "Oral Efficacy of a Respiratory Syncytial Virus Inhibitor in Rodent Models of Infection," *Antimicrobial Agents and Chemotherapy* 48(7):2448-2454.

Clements, J.D. (Jul. 1997). "Surface Warfare Against Pathogens Using Mucosal Vaccines," *Nature Biotech.* 15:622-623.

Clyde Jr., W.A. (Apr. 1980). "Experimental Models for Study of Common Respiratory Viruses," *Environmental Health Perspectives* 35:107-112.

Coley Pharmaceutical Group, Inc. (Oct. 30, 2002). "Coley Pharmaceutical Group Identifies New Class of CpG Oligonucleotides," Press Release located at <http://www.coleypharma.com/coley/pr_1036000898.html>, last visited on Apr. 11, 2007, two pages.

Coley Pharmaceutical Group, Inc. (Sep. 27, 2005). "Coley Pharmaceutical Group Initiates Second Phase Ib Clinical Study of ActilonTM for Treatment of HCV," Press Release located at <http://www.coleypharma.com/coley/pr_1127805994.html>, last visited on Apr. 11, 2007, two pages.

Coley Pharmaceutical Group, Inc. (Jan. 22, 2007). "Coley Pharmaceutical Group Updates Hepatitis C Drug Development Strategy," Press Release located at <http://www.coleypharma.com/coley/pr_20070122.html>, last visited on Apr. 11, 2007, three pages.

Coligan, J.E. et al., eds. (1998). *Current Protocols in Immunology* vol. 1, John Wiley &.Sons, Inc: pp. 1-9 (Table of Contents).

Cowdery, J.S. et al. (1996). "Bacterial DNA Induces NK Cells to Produce IFN-Gamma in Vivo and Increases the Toxicity of :Lipopolysaccharides" *J. Immunol.* 156:4570-4575.

Current Drugs Ltd. (Feb. 24, 2003). "Lilly and 3M Suspend Resiquimod Trials," located at <http://www.iddb.com/iddb3/iddb3_2/reports.print_display?i_query_id=0&template=Refe...>, last visited on Oct. 13, 2005, 1 page.

Current Drugs Ltd. (Feb. 24, 2003). "Preliminary Data From Recently Completed Clinical Trials of Resiquimod Suggest Dosing Used in Studies will not Achieve Adequate Efficacy," located at <http://www.iddb.com/iddb3/iddb3_2/reports.print_display?i_qury_id=0&template=Refe...>, last visited on Oct. 13, 2005, 1 page.

Dartmann et al. (1986). "The Nucleotide Sequence and Genome Organization of Human Papilloma Virus Type 11," *Virology* 151:124-130.

Davis, H. et al. (1998). "CpG DNA is a Potent Enhancer of Specific Immunity in Mice Immunized with Recombinant Hepatitis B Surface Antigen," *Journal of Immunology* 160(2):870-876.

Dolin, R. (1985). "Antiviral Chemotherapy and Chemoprophylaxis," *Science* 227:1296-1303.

Elkins, K.L. et al. (1999). "Bacterial DNA Containing CpG Motifs Stimulates Lymphocyte-Dependent Protection of Mice Against Lethal Infection with Intracellular Bacteria" *J. Immunol.* 162:2291-2298.

Equils, O. et al. (2003). "Toll-like Receptor 2 (TLR2) and TLR9 Signaling Resulted From HIV-Long Terminal Repeat *Trans*-Activation and HIV Replication in HIV-1 Transgenic Mouse Spleen Cells: Implications of Simultaneous Activation of TLRs on HIV Replication," *J. Immunol.* 170:5159-5164.

Fearon, K. et al. (2003). "A Minimal Human Immunostimulatory CpG Motif That Potently Induces IFN-Gamma and IFN-Alpha Production," *Eur. J. Immunol.* 33:2114-2212.

Final Office Action mailed on Sep. 24, 2002, for U.S. Appl. No. 09/802,686, filed Mar. 9, 2001, 10 pages.

Final Office Action mailed on Sep. 9, 2003, for U.S. Appl. No. 09/802,686, filed Mar. 9, 2001, 9 pages.

Final Office Action mailed on Jun. 16, 2006, for U.S. Appl. No. 09/802,686, filed Mar. 9, 2001, 20 pages.

Final Office Action mailed on Oct. 26, 2006, for U.S. Appl. No. 10/426,237, filed Jul. 28, 2009, 10 pages.

Final Office Action mailed on Aug. 21, 2007, for U.S. Appl. No. 09/802,686, filed Mar. 9, 2001, 18 pages.

Final Office Action mailed on Apr. 28, 2009, for U.S. Appl. No. 09/802,686, filed Mar. 9, 2001, 11 pages.

Freshney, R.I., ed. (1987). *Animal Cell Culture: A Practical Approach*, IRL Press: pp. vii-xii. (Table of Contents).
Gait, M. J., ed. (1984). *Oligonucleotide Synthesis: A Practical Approach* IRL Press: pp. vii-xii. (Table of Contents).
Gao, H. et al. (1995). "Circulation of Oligonucleotides by Disulfide Bridge Formation" *Nucleic Acids Res.* 23(11):2025-2029.
Godard, G. et al. (1995). "Antisense Effects of Cholesterol-Oligodeoxynucleotide Conjugates Associated with Poly(Alkylcyanoacrylate) Nanoparticles" *Eur. J. Biochem.* 232:404-410.
Gramzinski, R.A. et al. (1998). "Immune Response to a Hepatitis B DNA Vaccine in Aotus Monkeys: a Comparison of Vaccine Formulation, Route, and Method of Administration" *Mol. Med.* 4:109-118.
Guerrero-Plata, A. et al. (Aug. 2005). "Activity and Regulation of Alpha Interferon in Respiratory Syncytial Virus and Human Metapneumovirus Experimental Infections," *Journal of Virology* 79(16):10190-10199.
Hartmann, G. et al. (2000). "Mechanism and Function of a Newly Identified CpG DNA Motif in Human Primary B Cells," *J. Immunology* 164:944-952.
Hartmann, G. et al. (2000). "Delineation of a CpG Phosphorothioate Oligodeoxynucleotide for Activating Primate Immune Responses In Vitro and In Vivo," *J. Immunol.* 164(3):1617-1624.
Horner, A.A. et al. (1998). "Immunostimulatory DNA is a Potent Mucosal Adjuvant" *Cell. Immunol.* 190:77-82.
Infante-Duarte, C. et al. (1999). "Th1/Th2 Balance in Infection," *Springer Seminars in Immunopathology* 21(3):317-338.
International Search Report mailed Jun. 17, 2002 for PCT Application No. PCT/US01/07839 filed Mar. 12, 2001, 4 pages.
International Search Report mailed Jun. 17, 2002 for PCT Application No. PCT/US01/07840 filed Mar. 12, 2001, 4 pages.
International Search Report mailed Jun. 17, 2002 for PCT Application No. PCT/US01/07842 filed Mar. 12, 2001, 4 pages.
International Search Report mailed Jun. 17, 2002 for PCT Application No. PCT/US01/07931 filed Mar. 12, 2001, 5 pages.
International Search Report mailed Jun. 18, 2002 for PCT Application No. PCT/US01/07841 filed Mar. 12, 2001, 4 pages.
Jäger, A. et al. (1988). "Oligonucleotide N-Alkylphosphoramidates: Synthesis and Binding to Polynucleotides" *Biochem.* 27(19):7237-7246.
Jakob, T. et al. (1998). "Activation of Cutaneous Dendritic Cells by CpG-Containing Oligodeoxynucleotides: a Role for Dendritic Cells in the Augmentation of Th1 Responses by Immunostimulatory DNA" *J. Immunol.* 161:3042-3049.
Kang, S. et al. (Sep. 2004). "Intranasal Immunization with Inactivated Influenza Virus Enhances Immune Responses to Coadministered Simian-Human Immunodeficiency Virus-Like Particle Antigens," *Journ. of Vir.* 78(18):9624-9632.
Kataoka, T. et al. (1992). "Antitumor Activity of Synthetic Oligonucleotides with Sequences from cDNA Encoding Proteins of *Mycobacterium bovis* BCG" *Jpn. J. Cancer Res.* 83:244-247.
Kimura, Y. et al. (1994). "Binding of Oligoguanylate to Scavenger Receptors is Required for Oligonucleotides to Augment NK Cell Activity and Induce IFN" *J. Biochem.* (Tokyo) 116(5):991-994.
Kline, J. N. et al. (1997). "Immune Redirection by CpG Oligonucleotides Conversion of a Th2 Response to a Th1 Response in a Murine Model of Asthma" *J. Invest. Med.* 45(3):282A.
Klinman, D.M. et al. (1996). "CpG Motifs Present in Bacteria DNA Rapidly Induce Lymphocytes to Secrete Interleukin 6, Interleukin 12, and Interferon Gamma" *Proc. Natl. Acad. Sci. USA* 93:2879-2883.
Klinman, D.M. et al. (1997). "Contribution of CpG Motifs to the Immunogenicity of DNA Vaccines" *J. Immunol.* 158:3635-3639.
KMIEC. (1999). "Gene Therapy," *American Scientist* 87:240-247.
Kobayashi, H. et al. (1999). "Immunostimulatory DNA Prepriming: a Novel Approach for Prolonged Th1-Biased Immunity," *Cell Immun.* 198:69-75.
Kovarik, J. et al. (1999). "CpG Oligodeoxynucleotides can Circumvent the Th2 Polarization of Neonatal Responses to Vaccines but May Fail to Fully Redirect Th2 Responses Established by Neonatal Priming" *J. Immunol.* 162:1611-1617.
Krieg, A.M. (Aug. 1996). "An Innate Immune Defense Mechanism Based on the Recognition of CpG Motifs in Microbial DNA," *J. Lab. Clin. Med.* 128(2):128-133.
Krieg, A.M. (1996). "Lymphocyte Activation by CpG Dinucleotide Motifs in Prokaryotic DNA" *Trends Microbiol.* 4(2):73-77.
Krieg, A.M. (1998). "Leukocyte Stimulation by Oligodeoxynucleotides" Chapter 24 in *Applied Antisense Oligonucleotide Technology* C.A. Stein et al. eds. Wiley-Liss, Inc.: pp. 431-448.
Krieg, A.M. (1999). "CpG DNA: a Novel Immunomodulator" *Trends Microbiol.* 7(2):64-65.
Krieg, A.M. (1999). "Direct Immunologic Activities of CpG DNA and Implications for Gene Therapy," *The Journal of Gene Medicine* 1:56-63.
Krieg, A.M. (2000). "The Role of CpG Motifs in Innate Immunity," *Current Opinion in Immunology* 12:35-43.
Krieg, A.M. et al. (1989). "A Role for Endogenous Retroviral Sequences in the Regulation of Lymphocyte Activation" *J. Immunol.* 143(8):2448-2451.
Krieg, A.M. et al. (1995). "CpG Motifs in Bacterial DNA Trigger Direct B-Cell Activation" *Nature* 374:546-549.
Krieg, A.M. et al. (1996). "Oligodeoxynucleotide Modifications Determine the Magnitude of B Cell Stimulation by CpG Motifs" *Antisense Nucleic Acid Drug Dev.* 6:133-139.
Krieg, A.M. et al. (1998a). "The Role of CpG Dinucleotides in DNA Vaccines" *Trends Microbiol.* 6(1):23-27.
Krieg, A.M. et al. (1998b). "CpG DNA Induces Sustained IL-12 Expression in Vivo and Resistance to *Listeria monocytogenes* Challenge" *J. Immunol.* 161:2428-2434.
Krieg, A.M. et al. (1998c). "Sequence Motifs in Adenoviral DNA Block Immune Activation by Stimulatory CpG Motifs" *Proc. Natl. Acad. Sci. USA* 95:12631-12636.
Krieg, A.M. et al. (2002). "CpG Motifs in Bacterial DNA and Their Immune Effects," *Annu. Rev. Immunol.* 20:709-760.
Ksiazek, T.G. et al. (May 15, 2003). "A Novel Coronavirus Associated with Severe Acute Respiratory Syndrome," *N. Engl. J. Med.* 348(20):1953-1966.
Kwant, A. et al. (2004). "Intravaginal Immunization with Viral Subunit Protein Plus CpG Oligodeoxynucleotides Induces Protective Immunity Against HSV-2," *Vaccine* 22:3098-3104.
Latimer, L.J.P. et al. (1995). "Specificity of Monoclonal Antibodies Produced Against Phosphorothioate and Ribo Modified DNAs" *Mol. Immunol.* 32(14/15):1057-1064.
Leclerc, C. et al. (1997). "The Preferential Induction of a Th1 Immune Response by DNA-Based Immunization is Mediated by the Immunostimulatory Effect of Plasmid DNA" *Cell. Immunol.* 179:97-106.
Liang, H. et al. (1996). "Activation of Human B Cells by Phosphorothioate Oligodeoxynucleotides" *J. Clin. Invest.* 98(5):1119-1129.
Lipford, G.B. et al. (1997a). "CpG-Containing Synthetic Oligonucleotides Promote B and Cytotoxic T Cell Responses to Protein Antigen: A New Class of Vaccine Adjuvants" *Eur. J. Immunol.* 27:2340-2344.
Lipford, G.B. et al. (1997b). "Immunostimulatory DNA: Sequence-Dependent Production of Potentially Harmful or Useful Cytokines" *Eur. J. Immunol.* 27:3420-3426.
Liu, H.-M. et al. (1998). "Immunostimulatory CpG Oligodeoxynucleotides Enhance the Immune Response to Vaccine Strategies Involving Granulocyte-Macrophage Colony-Stimulating Factor" *Blood* 92(10):3730-3736.
MacFarlane, D.E. et al. (1997). "Unmethylated CpG-Containing Oligodeoxynucleotides Inhibit Apoptosis in WEHI 231 B Lymphocytes Induced by Several Agents: Evidence for Blockade of Apoptosis at a Distal Signalling Step" *Immunology* 91:586-593.
Maggon, K. et al. (2004). "New Drugs and Treatment for Respiratory Syncytial Virus," *Rev. Med. Virol.* 14:149-168.
Manzel, L. et al. (1999). "Lack of Immune Stimulation by Immobilized CpG-Oligodeoxynucleotide" *Antisense Nucl. Acid Drug Dev.* 9:459-464.
Marshall, E. (1995). "Gene Therapy's Growing Pains," *Science* 269:1050-1055.
Marshall, J.D. (2003). "Novel Chimeric Immunomodulatory Compounds Containing Short CpG Oligodeoxyribonucleotides Have Differential Activities in Human Cells," *Nucleic Acids Research* 31(17):5122-5133.

Marshall, J.D. et al. (2005). "Superior Activity of the Type C Class of ISS In Vitro and In Vivo Across Multiple Species," *DNA and Cell Bio.* 24(2):63-72.

Martin-Orozco, E. et al. (1999). "Enhancement of Antigen-Presenting Cell Surface Molecules Involved in Cognate Interactions by Immunostimulatory DNA Sequences" *Int. Immunol.* 11 (7): 1111-1118.

Masihi, K.N. (Jul. 2001). "Fighting Infection Using Immunomodulatory Agents," *Expert Opin. Biol. Ther.* 1(4):641-653.

Masseyeff, R.F., ed. (1993). *Methods of Immunological Analysis*. vol. 1: Fundamentals. Verlagsgesellschaft mbH, D-6940: Weinheim, Germany: pp. xi-xxii (Table of Contents).

Matteucci, M. (1997). "Oligonucleotide Analogs: an Overview" in *Oligonucleotides as Therapeutic Agents*, (CIBA Foundation Symposium 209) John Wiley and Sons, New York, NY: pp. 5-18.

McCluskie, M.J. et al. (1998). "CpG DNA is a Potent Enhancer of Systemic and Mucosal Immune Responses Against Hepatitis B Surface Antigen with Intranasal Administration to Mice" *J. Immunol.* 161:4463-4466.

McHutchinson, J.G. et al. (Apr. 2006). "Early Viral Response to New HCV Drug CPG 10101 Toll-Receptor Antagonist, in Combination with Pegylated Interferon and/or Ribavirin, in Chronic HCV Genotype 1 Infected Patients with Prior Relapse Response," *41st Meeting of the European Association for the Study of Liver Diseases*, Vienna, Austria, Apr. 26-30, 2006, located at <http://www.natap.org/2006/Easl/EASL_24.htm>, last visited on Apr. 11, 2007, eight pages.

McHutchinson, J.G. et al. (Apr. 2006). "Randomized, Placebo-Controlled, Dose-Escalation Trial of New HCV Drug CPG 10101 Toll-Receptor Antagonist in Patients with Chronic Hepatitis C Virus," *41st Meeting of the European Association for the Study of Liver Diseases*, Vienna, Austria, Apr. 26-30, 2006, located at <http://www.natap.org/2006/Easl/EASL_23.htm>, last visited on Apr. 11, 2007, eleven pages.

Merriam-Webster, Inc. (1983). *Webster's Ninth New Collegiate Dictionary*, Merriam-Webster, Inc.: Springfield, MA, p. 57.

Miller, J.H. et al., eds. (1987). "Gene Transfer Vectors for Mammalian Cells" in *Current Communications in Molecular Biology*. Cold Spring Harbor Laboratory: pp. vii-ix (Table of Contents).

Miller, P.S. et al. (1971). "Syntheses and Properties of Adenine and Thymine Nucleoside Alkyl Phosphotriesters, the Neutral Analogs of Dinucleoside Monophosphates" *JACS* 93(24):6657-6665.

Mojcik, C.F. et al. (1993). "Administration of a Phosphorothioate Oligonucleotide Antisense to Murine Endogenous Retroviral MCF Env Causes Immune Effects in Vivo in a Sequence-Specific Manner" *Clin. Immunol. and Immunopathol.* 67(2):130-136.

Moldoveanu, Z. et al. (1998). "CpG DNA, a Novel Immune Enhancer for Systemic and Mucosal Immunization with Influenza Virus" *Vaccine* 16(11/12):1216-1224.

Mountain. (2000). "Gene Therapy: The First Decade," *TIBTECH* 18:119-128.

Mullis, K.B. et al., eds. (1994). *PCR: The Polymerase Chain Reaction*. Birkhäuser: pp. xv-xvii (Table of Contents).

Murakami, M. et al. (1999). "Human Papillomavirus Vaccines for Cervical Cancer," *J. Immunother.* 22(3):212-218.

Mutwiri, G. et al. (2003). "Biological Activity of Immunostimulatory CpG DNA Motifs in Domestic Animals," *Veterinary Immunology and Immunopathology* 91:89-103.

Nelson, J.S. et al. (1997). "N3'→P5' Oligodeoxyribonucleotide Phosphoramidates: A New Method of Synthesis Based on a Phosphoramidite Amino-Exchange Reaction" *J. Org. Chem.* 62:7278-7287.

Non-Final Office Action mailed on Dec. 28, 2001, for U.S. Appl. No. 09/802,686, filed Mar. 9, 2001, 7 pages.

Non-Final Office Action mailed on Mar. 20, 2003, for U.S. Appl. No. 09/802,686, filed Mar. 9, 2001, 11 pages.

Non-Final Office Action mailed on Apr. 23, 2004, for U.S. Appl. No. 09/802,686, filed Mar. 9, 2001, 8 pages.

Non-Final Office Action mailed on Nov. 30, 2004, for U.S. Appl. No. 09/802,686, filed Mar. 9, 2001, 12 pages.

Non-Final Office Action mailed on Oct. 18, 2005, for U.S. Appl. No. 09/802,686, filed Mar. 9, 2001, 11 pages.

Non-Final Office Action mailed on Feb. 13, 2006, for U.S. Appl. No. 10/426,237, filed Jul. 28, 2009, 10 pages.

Non-Final Office Action mailed on Jan. 26, 2007, for U.S. Appl. No. 09/802,686, filed Mar. 9, 2001, 23 pages.

Non-Final Office Action mailed on Jan. 23, 2008, for U.S. Appl. No. 09/802,686, filed Mar. 9, 2001, 20 pages.

Non-Final Office Action mailed on Oct. 16, 2008, for U.S. Appl. No. 09/802,686, filed Mar. 9, 2001, 9 pages.

Olbrich, A.R.M. et al. (Oct. 2003). "Preinfection Treatment of Resistant Mice With CpG Oligonucleotides Renders Them Susceptible to Friend Retrovirus-Induced Leukemia," *J. Virol.* 77:10658-10662.

Orkin et al. (1995). Report and Recommendations of the Panel to Assess the NIH Investment in Research on Gene Therapy, 33 pages.

Peyrottes, S. et al. (1996). "Oligodeoxynucleoside Phosphoramidates (P-NH2): Synthesis and Thermal Stability of Duplexes with DNA and RNA Targets" *Nucleic Acids Res.* 24(10):1841-1848.

Pisani, P. et al. (1993). "Estimates of the Worldwide Mortality from Eighteen Major Cancers in 1985. Implications for Prevention and Projections of Future Burden," *Intl. J. Cancer* 55:891-903.

Pisetsky, D.S. (1996a). "The Immunologic Properties of DNA" *J. Immunol.* 156(2):421-423.

Pisetsky, D.S. (1996b). "Immune Activation by Bacterial DNA: a New Genetic Code" *Immunity* 5:303-310.

Pisetsky, D.S. et al. (1994). "Stimulation of Murine Lymphocyte Proliferation by a Phosphorothioate Oligonucleotide with Antisense Activity for Herpes Simplex Virus" *Life Sci.* 54(2):101-107.

Pisetsky, D.S. et al. (1995). "Immunological Properties of Bacterial DNA" *Ann. N.Y. Acad. Sci.* 772:152-163.

Prince, G.A. (Summer 1994). "The Cotton Rat in Biomedical Research," Animal Welfare Information Center Newsletter 5(2), located at <http:/www.nal.usda.gov/awic/newsletters/v5n2/5n2princ.html>, last visited on Feb. 16, 2006, six pages.

Raz, E. et al. (1994). "Intradermal Gene Immunization: the Possible Role of DNA Uptake in the Induction of Cellular Immunity to Viruses" *Proc. Natl. Acad. Sci. USA* 91:9519-9523.

Raz, E. et al. (1996). "Preferential Induction of a Th1 Immune Response and Inhibition of Specific IgE Antibody Formation by Plasmid DNA Immunization" *Proc. Natl. Acad. Sci. USA* 93:5141-5145.

Redford, T.W. et al. (1998). "Cyclosporin A Enhances IL-12 Production by CpG Motifs in Bacterial DNA and Synthetic Oligodeoxynucleotides" *J. Immunol.* 161:3930-3935.

Rhodes et al., eds. (1953). *Textbook of Virology*, 2nd ed., Williams and Wilkins: pp. 66-69.

Romagnani, S. (2000). "T-Cell Subsets (Th1 versus Th2)" *Ann. Allergy Asthma Immunol.* 85(1):9-18.

Roman, M. et al. (1997). "Immunostimulatory DNA Sequences Function as T Helper-1-Promoting Adjuvants" *Nature Med.* 3(8):849-854.

Romano et al. (2000). "Latest Developments in Gene Transfer Technology: Achievements, Perspectives, and Controversies over Therapeutic Applications," *Stem Cell* 18:19-39.

Sakao, Y. et al. (1999). "IL-18-deficient Mice are Resistant to Endotoxin-Induced Liver Injury but Highly Susceptible to Endotoxin Shock," *Int Immunol.* 11(3):471-480.

Sambrook, J. et al., eds. (1989). *Molecular Cloning: A Laboratory Manual*, Second Edition, Cold Spring Harbor Laboratory Press: pp. x-xxxviii (Table of Contents).

Sato, Y. et al. (1996). "Immunostimulatory DNA Sequences Necessary for Effective Intradermal Gene Immunization" *Science* 273:352-354.

Schacht, E. et al. (1996). "Biomedical Applications of Degradable Polyphosphazenes" *Biotechnol. Bioeng.* 52:102-107.

Schultz, L. (Apr. 2004). "Some Model Organisms Mightier Than the Mouse," *Drug Discov. and Devel.* 7(4):40-44.

Schultz, R.G. et al. (1996). "Oligo-2'-Fluoro-2'-Deoxynucleotide N3'→P5 Phosphoramidates: Synthesis and Properties" *Nucleic Acids Res.* 24(15):2966-2973.

Schwartz, D.A. et al. (1997). "CpG Motifs in Bacterial DNA Cause Inflammation in the Lower Respiratory Tract" *J. Clin. Invest.* 100(1):68-73.

Seo, S.H. et al. (Sep. 2002). "Lethal H5N1 Influenza Viruses Escape Host Anti-viral Cytokine Responses," *Nature Medicine* 8(9):950-954.

Shigeta, S. (1998). "Approaches to Antiviral Chemotherapy for Acute Respiratory Infections," *Antiviral Chemistry and Chemotherapy* 9:93-107.

Shimada, S. et al. (1986). "In Vivo Augmentation of Natural Killer Cell Activity with a Deoxyribonucleic Acid Fraction of BCG" *Jpn. J. Cancer Res.* 77:808-816.

Silverman, E.S. et al. (2003). "Immunostimulatory DNA for Asthma: Better Than Eating Dirt," *Am. J. Respr. Cell Mol. Biol.* 28:645-647.

Smith, V.P. et al. (Feb. 2002). "Inhibition of Interferons by Ectromelia Virus," *Journal of Virology* 76(3):1124-1134.

Sonehara, K. et al. (1996). "Hexamer Palindromic Oligonucleotides with 5'-CG-3' Motif(s) Induce Production of Interferon" *J. Interferon and Cytokine Res.* 16:799-803.

Sparwasser, T. et al. (1997). "Macrophages Sense Pathogens Via DNA Motifs: Induction of Tumor Necrosis Factor-Alpha-Mediated Shock" *Eur. J. Immunol.* 27:1671-1679.

Spiegelberg, H.L. et al. (1998). "Inhibition of IgE Formation and Allergic Inflammation by Allergen Gene Immunization and by CpG Motif Immunostimulatory Oligodeoxynucleotides" *Allergy* 53:93-97.

Spiegelberg, H.L. et al. (1999). "Inhibition of Allergic Inflammation in the Lung by Plasmid DNA Allergen Immunization" *Pediatr. Pulmonol.* Suppl. 18:118-121.

Stacey, K.J. et al. (1996). "Macrophages Ingest and are Activated by Bacterial DNA" *J. Immunol.* 157(5):2116-2122.

Stein, C.A. et al. (1997). "Non-Antisense Effects of Oligodeoxynucleotides" Chapter 11 in *Antisense Technology* Lichtenstein, C. and Nellen, W. eds., IRL Press: pp. 241-264.

Stirchak, E.P. et al. (1989). "Uncharged Stereoregular Nucleic Acid Analogs: 2. Morpholino Nucleoside Oligomers with Carbamate Internucleoside Linkages" *Nucleic Acids Res.* 17(15):6129-6141.

Stratagene. (1988). *Catalog: Gene Characterization Kits*, p. 39. (Table of Contents).

Sundaram et al. (1998). "Intracutaneous Vaccination of Rabbits with the E6 Gene of Cottontail Rabbit Papillomavirus Provides Partial Protetion Against Virus Challenge," *Vaccine* 16(6):613-623.

Tokunaga et al. (1999). "How BCG Led to the Discovery of Immunostimulatory DNA," *Jpn. J. Infec. Dis.* 52:1-11.

Tokunaga, T. et al. (1992). "Synthetic Oligonucleotides with Particular Base Sequences from the cDNA Encoding Proteins of *Mycobacterium bovis* BCG Induce Interferons and Activate Natural Killer Cells" *Microbiol. Immunol.* 36(1):55-66.

Unknown. (Date Unknown). "Resiquimod (Topical), 3M," located at <http://www.iddb.com/iddb3/iddb3_2/reports.print_display?i_query_id=5874091&template...>, last visited on Oct. 7, 2005, 1 page.

Van Nest, G. et al. (1999). "An Immunostilmulatory Oligonucleotide (ISS ODN) Enhances Immune Responses to HBV Vaccine in a Varieety of Aminal Species Including Primates," Abstracts of the 39th Interscience Conference of Anitmicrobial Agents and Chemotherapy, San Francisco, California, p. 374, abstract No. 679.

Verma, et al. (1997). "Gene Therapy—Promises, Problems and Prospects," *Nature* 389:239-242.

Wang, S. et al. (1994). "Circular RNA Oligonucleotides. Synthesis, Nucleic Acid Binding Properties, and a Comparison with Circular DNAs" *Nucleic Acids Res.* 22(12):2326-2333.

Warner, B.D. et al. (1984). "Construction and Evaluation of an Instrument for the Automated Synthesis of Oligodeoxyribonucleotides" *DNA* 3(5):401-411.

Weeratna, R. et al. (1998). "Reduction of Antigen Expression from DNA Vaccines by Coadministered Oligodeoxynucleotides" *Antisense and Nucleic Acid Drug Development* 8:351-356.

Weiner, G.J. et al. (1997). "Immunostimulatory Oligodeoxynucleotides Containing the CpG Motif are Effective as Immune Adjuvants in Tumor Antigen Immunization" *Proc. Natl. Acad. Sci. USA* 94:10833-10837.

Weir, D.M., ed., *Handbook of Experimental Immunology in Four Volumes* "Volume 4: Applications of Immunological Methods in Biomedical Sciences" Blackwell Scientific Publications: pp. v-x (Table of Contents), Jan. 15, 1996.

Wild, D., ed., (1994). *The Immunoassay Handbook*, Stockton Press: pp. v-xvi (Table of Contents).

Wooldridge, J.E. et al. (1997). "Immunostimulatory Oligodeoxynucleotides Containing CpG Motifs Enhance the Efficacy of Monoclonal Antibody Therapy of Lymphoma" *Blood* 89(8):2994-2998.

Wyde, P.R. et al. (1995). "Evaluation of the Protective Efficacy of Reshaped Human Monoclonal Antibody RSHZ19 Against Respiratory Syncytial Virus in Cotton Rats," *Pediatr. Res.* 38(4):543-550.

Yamamoto, S. et al. (1992). "Unique Palindromic Sequences in Synthetic Oligonucleotides are Required to Induce IFN [correction of INF] and Augment IFN-Mediated [correction of INF] Natural Killer Activity" *J. Immunol.* 148(12):4072-4076.

Yamamoto, T. et al. (1994a). "Ability of Oligonucleotides with Certain Palindromes to Induce Interferon Production and Augment Natural Killer Cell Activity is Associated with Their Base Length" *Antisense Research and Development* 4:119-122.

Yamamoto, T. et al. (Aug. 1994b). "Synthetic Oligonucleotides with Certain Palindromes Stimulate Interferon Production of Human Peripheral Blood Lymphocytes in Vitro" *Jpn. J. Cancer Res.* 85:775-779.

Yamamoto, S. et al. (2000). "Oligodeoxyribonucleotides With 5'-ACGT-3' or 5'-TCGA-3' Sequence Induce Production of Interferons," in *Current Topics in Microbiology and Immunology*, Compans, R.W. et al. eds., Springer-Verlag: Berlin, Germany, pp. 23-39.

Yi, A.-K. et al. (1996). "IFN-Gamma Promotes IL-6 and IgM Secretion in Response to CpG Motifs in Bacterial DNA and Oligodeoxynucleotides" *J. Immunol.* 156(2):558-564.

Yi, A.-K. et al. (1998a). "CpG DNA Rescue from Anti-IgM-Induced WEHI-231 B Lymphoma Apoptosis Via Modulation of I Kappa B Alpha and I Kappa B Beta and Sustained Activation of Nuclear Factor-Kappa B/c-Rel" *J. Immunol.* 160(3):1240-1245.

Yi, A.-K. et al.(1998b). "CpG Motifs in Bacterial DNA Activate Leukocytes Through the pH-Dependent Generation of Reactive Oxygen Species" *J. Immunol.* 160(10):4755-4761.

Yi, A.-K. et al. (1998c). "CpG Oligodeoxyribonucleotides Rescue Mature Spleen B Cells from Spontaneous Apoptosis and Promote Cell Cycle Entry" *J. Immunol.* 160(12):5898-5906.

Yi, A.-K. et al. (1998d). "Rapid Induction of Mitogen-Activated Protein Kinases by Immune Stimulatory CpG DNA" *J. Immunol.* 161(9):4493-4497.

Zaitseva, M. et al. (Nov. 1, 2000). "Interferon γ and Interleukin 6 Modulate the Susuceptibility of Macrophages to Human Immunodeficiency Virus Type 1 Infection," *Blood* 96(9):3109-3117.

Zhao, Q. et al. (1996). "Effect of Different Chemically Modified Oligodeoxynucleotides on Immune Stimulation" *Biochem. Pharmacol.* 51(2):173-182.

Zimmerman, S. et al. (1998). "CpG Oligodeoxynucleotides Trigger Protective and Curative Th1 Responses in Lethal Murine Leishmaniasis" *J. Immunol.* 160(8):3627-3630.

Zon, G. (1993). "Oligonucleoside Phosphorothioates" Chapter 8 in *Protocols for Oligonucleotides and Analogs, Synthesis and Properties*, Agrawal (ed.), Humana Press: pp. 165-189.

Wang, Y. et al. (Nov. 2005). "The Toll-Like Receptor 7 (TLR7) Agonist, Imiquimod, and the TLR9 Agonist, CpG ODN, Induce Antiviral Cytokines and Chemokines but Do Not Prevent Vaginal Transmission of Simian Immunodeficiency Virus When Applied Intravaginally to Rhesus Macaques," *Journal of Virology* 79(22):14355-14370.

* cited by examiner

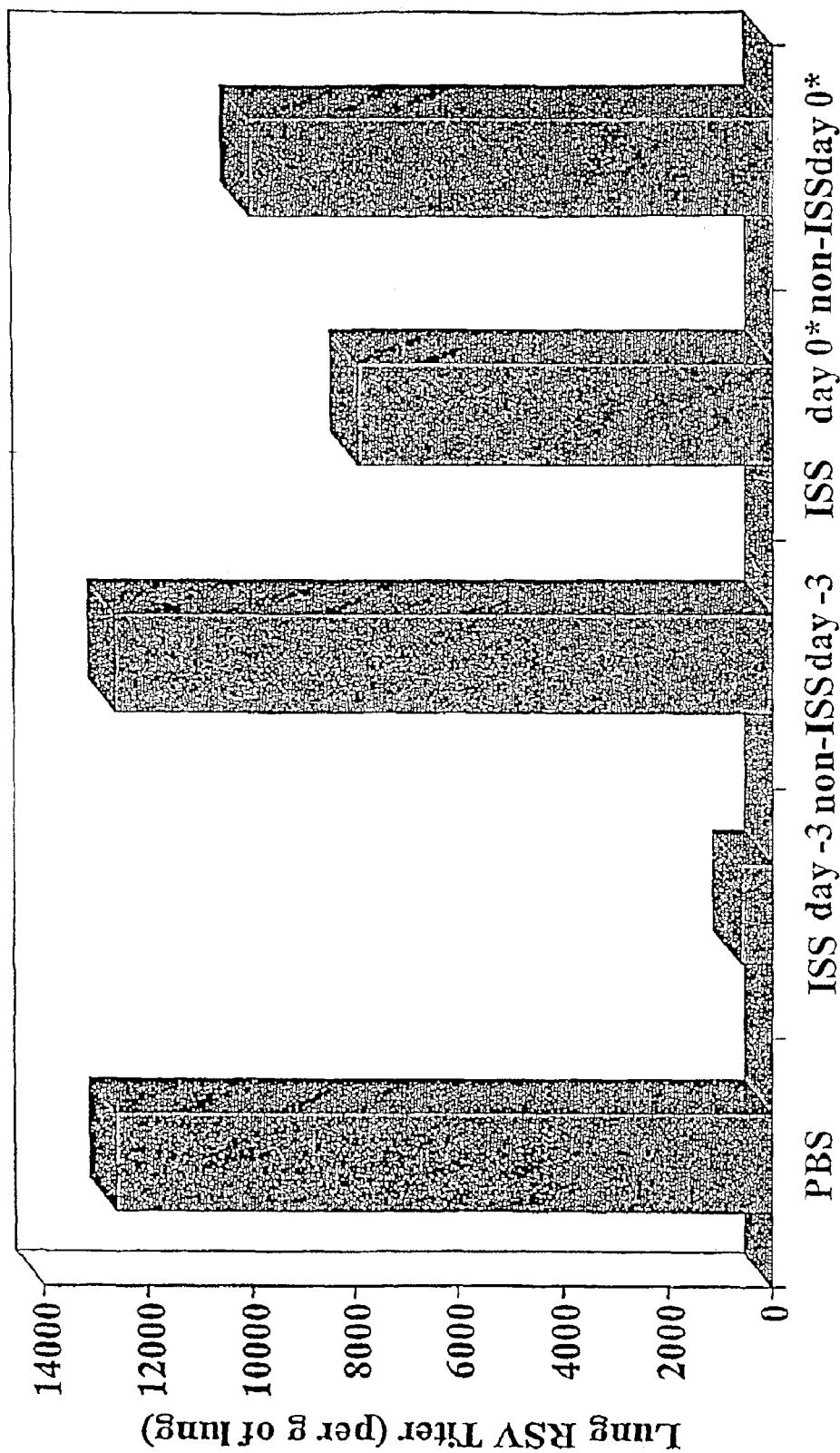

METHODS OF PREVENTING AND TREATING RESPIRATORY VIRAL INFECTION USING IMMUNOMODULATORY POLYNUCLEOTIDE SEQUENCES

CROSS-REFERENCE TO RELATED APPLICATIONS

This application is a continuation of U.S. application Ser. No. 09/802,686, filed on Mar. 9, 2001, which claims the priority benefit of U.S. Provisional Application 60/188,583, filed Mar. 10, 2000, which are hereby incorporated herein by reference in their entirety.

TECHNICAL FIELD

The invention is in the field of immunostimulatory polynucleotides, more particularly their use in ameliorating or preventing respiratory viral infection and symptoms of respiratory viral infection.

BACKGROUND ART

Despite massive research efforts to find cures, respiratory virus infection remains a major health problem worldwide. Influenza and rhinovirus are causative agents for flu and common cold, respectively, lead to significant lost productivity annually as well as discomfort and even death due to illness. While many over-the-counter remedies are available, these drugs merely treat symptoms, often with only limited success, leaving the patient still debilitated from the infection. Respiratory syncytial virus (RSV) is a leading cause of serious lower respiratory tract infections and children under two years and has more recently been identified as an important cause of lower respiratory tract infection in adults. No vaccines are currently available for preventing RSV infection. The only antiviral currently approved for treatment of the disease, ribavirin, suffers from the drawbacks of being licensed only for administration as continuous small particle aerosol and being a potential teratogen. A challenge facing treatment of these infections is to discover an anti-viral agent which effectively suppresses viral infection, while not producing unpleasant and unacceptable side-effects.

Administration of certain DNA sequences, generally known as immunostimulatory sequences or "ISS," induces an immune response with a Th1-type bias as indicated by secretion of Th1-associated cytokines. The Th1 subset of helper cells is responsible for classical cell-mediated functions such as delayed-type hypersensitivity and activation of cytotoxic T lymphocytes (CTLs), whereas the Th2 subset functions more effectively as a helper for B-cell activation. The type of immune response to an antigen is generally influenced by the cytokines produced by the cells responding to the antigen. Differences in the cytokines secreted by Th1 and Th2 cells are believed to reflect different biological functions of these two subsets. See, for example, Romagnani (2000) *Ann. Allergy Asthma Immunol.* 85:9-18.

Administration of an immunostimulatory polynucleotide with an antigen results in a Th1-type immune response to the administered antigen. Roman et al. (1997) *Nature Med.* 3:849-854. For example, mice injected intradermally with *Escherichia coli* (*E. coli*) β-galactosidase (β-Gal) in saline or in the adjuvant alum responded by producing specific IgG1 and IgE antibodies, and CD4$^+$ cells that secreted IL-4 and IL-5, but not IFN-γ, demonstrating that the T cells were predominantly of the Th2 subset. However, mice injected intradermally (or with a tyne skin scratch applicator) with plasmid DNA (in saline) encoding β-Gal and containing an ISS responded by producing IgG2a antibodies and CD4$^+$ cells that secreted IFN-γ, but not IL-4 and IL-5, demonstrating that the T cells were predominantly of the Th1 subset. Moreover, specific IgE production by the plasmid DNA-injected mice was reduced 66-75%. Raz et al. (1996) *Proc. Natl. Acad. Sci. USA* 93:5141-5145. In general, the response to naked DNA immunization is characterized by production of IL-2, TNFα and IFN-γ by antigen-stimulated CD4$^+$ T cells, which is indicative of a Th1-type response. This is particularly important in treatment of allergy and asthma as shown by the decreased IgE production. The ability of immunostimulatory polynucleotides to stimulate a Th1-type immune response has been demonstrated with bacterial antigens, viral antigens and with allergens (see, for example, WO 98/55495).

Other references describing ISS include: Krieg et al. (1989) *J. Immunol.* 143:2448-2451; Tokunaga et al. (1992) *Microbiol. Immunol.* 36:55-66; Kataoka et al. (1992) *Jpn. J. Cancer Res.* 83:244-247; Yamamoto et al. (1992) *J. Immunol.* 148:4072-4076; Mojcik et al. (1993) *Clin. Immuno. and Immunopathol.* 67:130-136; Branda et al. (1993) *Biochem. Pharmacol.* 45:2037-2043; Pisetsky et al. (1994) *Life Sci.* 54(2):101-107; Yamamoto et al. (1994a) *Antisense Research and Development.* 4:119-122; Yamamoto et al. (1994b) *Jpn. J. Cancer Res.* 85:775-779; Raz et al. (1994) *Proc. Natl. Acad. Sci. USA* 91:9519-9523; Kimura et al. (1994) *J. Biochem.* (Tokyo) 116:991-994; Krieg et al. (1995) *Nature* 374:546-549; Pisetsky et al. (1995) *Ann. N.Y. Acad. Sci.* 772:152-163; Pisetsky (1996a) *J. Immunol.* 156:421-423; Pisetsky (1996b) *Immunity* 5:303-310; Zhao et al. (1996) *Biochem. Pharmacol.* 51:173-182; Yi et al. (1996) *J. Immunol.* 156:558-564; Krieg (1996) *Trends Microbiol.* 4(2):73-76; Krieg et al. (1996) *Antisense Nucleic Acid Drug Dev.* 6:133-139; Klinman et al. (1996) *Proc. Natl. Acad. Sci. USA.* 93:2879-2883; Raz et al. (1996); Sato et al. (1996) *Science* 273:352-354; Stacey et al. (1996) *J. Immunol.* 157:2116-2122; Ballas et al. (1996) *J. Immunol.* 157:1840-1845; Branda et al. (1996) *J. Lab. Clin. Med.* 128:329-338; Sonehara et al. (1996) *J. Interferon and Cytokine Res.* 16:799-803; Klinman et al. (1997) *J. Immunol.* 158:3635-3639; Sparwasser et al. (1997) *Eur. J. Immunol.* 27:1671-1679; Roman et al. (1997); Carson et al. (1997) *J. Exp. Med.* 186:1621-1622; Chace et al. (1997) *Clin. Immunol. and Immunopathol.* 84:185-193; Chu et al. (1997) *J. Exp. Med.* 186:1623-1631; Lipford et al. (1997a) *Eur. J. Immunol.* 27:2340-2344; Lipford et al. (1997b) *Eur. J. Immunol.* 27:3420-3426; Weiner et al. (1997) *Proc. Natl. Acad. Sci. USA* 94:10833-10837; Macfarlane et al. (1997) *Immunology* 91:586-593; Schwartz et al. (1997) *J. Clin. Invest.* 100:68-73; Stein et al. (1997) *Antisense Technology*, Ch. 11 pp. 241-264, C. Lichtenstein and W. Nellen, Eds., IRL Press; Wooldridge et al. (1997) *Blood* 89:2994-2998; Leclerc et al. (1997) *Cell. Immunol.* 179:97-106; Kline et al. (1997) *J. Invest. Med.* 45(3):282A; Yi et al. (1998a) *J. Immunol.* 160:1240-1245; Yi et al. (1998b) *J. Immunol.* 160:4755-4761; Yi et al. (1998c) *J. Immunol.* 160:5898-5906; Yi et al. (1998d) *J. Immunol.* 161:4493-4497; Krieg (1998) *Applied Antisense Oligonucleotide Technology* Ch. 24, pp. 431-448, C. A. Stein and A. M. Krieg, Eds., Wiley-Liss, Inc.; Krieg et al. (1998a) *Trends Microbiol.* 6:23-27; Krieg et al. (1998b) *J. Immunol.* 161:2428-2434; Krieg et al. (1998c) *Proc. Natl. Acad. Sci. USA* 95:12631-12636; Spiegelberg et al. (1998) *Allergy* 53(45S):93-97; Horner et al. (1998) *Cell Immunol.* 190:77-82; Jakob et al. (1998) *J. Immunol.* 161:3042-3049; Redford et al. (1998) *J. Immunol.* 161:3930-3935; Weeratna et al. (1998) *Antisense & Nucleic Acid Drug Development* 8:351-356; McCluskie et al. (1998) *J. Immunol.* 161(9):4463-4466; Gramzinski et al. (1998) *Mol. Med.* 4:109-118; Liu et al.

(1998) *Blood* 92:3730-3736; Moldoveanu et al. (1998) *Vaccine* 16: 1216-1224; Brazolot Milan et al. (1998) *Proc. Natl. Acad. Sci. USA* 95:15553-15558; Briode et al. (1998) *J. Immunol.* 161:7054-7062; Briode et al. (1999) *Int. Arch. Allergy Immunol.* 118:453-456; Kovarik et al. (1999) *J. Immunol.* 162:1611-1617; Spiegelberg et al. (1999) *Pediatr. Pulmonol. Suppl.* 18:118-121; Martin-Orozco et al. (1999) *Int. Immunol.* 11:1111-1118; EP 468,520; WO 96/02555; WO 97/28259; WO 98/16247; WO 98/18810; WO 98/37919; WO 98/40100; WO 98/52581; WO 98/55495; WO 98/55609 and WO 99/11275. See also Elkins et al. (1999) *J. Immunol.* 162:2291-2298, WO 98/52962, WO 99/33488, WO 99/33868, WO 99/51259 and WO 99/62923. See also Zimmermann et al. (1998) *J. Immunol.* 160:3627-3630; Krieg (1999) *Trends Microbiol.* 7:64-65; U.S. Pat. Nos. 5,663,153, 5,723,335, 5,849,719 and 6,174,872. See also WO 99/56755, WO 00/06588, WO 00/16804; WO 00/21556; WO 00/67023 and WO 01/12223.

There remains a serious need to develop effective therapies and preventive strategies for respiratory viruses.

All publications and patent applications cited herein are hereby incorporated by reference in their entirety.

DISCLOSURE OF THE INVENTION

The invention provides methods of suppressing, ameliorating, and/or preventing viral infection by a respiratory virus in an individual (either before or after exposure or infection) using immunostimulatory polynucleotide sequences. Accordingly, in one aspect, the invention provides methods of preventing, palliating, ameliorating, reducing and/or eliminating one or more symptoms of respiratory virus infection without administering a respiratory virus antigen. A polynucleotide comprising an immunostimulatory sequence (an "ISS") is administered to an individual who is at risk of being exposed to respiratory virus, has been exposed to respiratory virus or is infected with respiratory virus. The ISS-containing polynucleotide is administered without any respiratory virus antigens (i.e., respiratory virus antigen is not co-administered). Administration of the ISS results in reduced incidence and/or severity of one or more symptoms of respiratory virus infection.

In one embodiment, the invention provides methods of preventing a symptom of respiratory virus infection in an individual at risk of being exposed to a respiratory virus which entail administering an effective amount of a composition comprising a polynucleotide comprising an immunostimulatory sequence (ISS) (i.e., an amount of the composition sufficient to prevent a symptom of respiratory virus infection) to the individual, wherein the ISS comprises the sequence 5'-C, G-3' and wherein respiratory virus antigen is not administered in conjunction with administration of the composition (i.e., antigen is not administered with the ISS-containing polynucleotide), thereby preventing a symptom of respiratory virus infection.

Another embodiment of the invention provides methods of preventing a symptom of respiratory virus infection in an individual which entail administering an effective amount of a composition comprising a polynucleotide comprising an ISS to the individual, wherein the ISS comprises the sequence 5'-C, G-3' and wherein respiratory virus antigen is not administered in conjunction with administration of the composition, thereby preventing a symptom of respiratory virus infection. The individual may have been exposed to or infected by a respiratory virus.

Another embodiment of the invention provides methods of suppressing a respiratory virus infection in an individual which entail administering a composition comprising a polynucleotide comprising an ISS to the individual in an amount sufficient to reduce viral titer of the respiratory virus in a biological sample from the individual, wherein the ISS comprises the sequence 5'-C, G-3' and wherein respiratory virus antigen is not administered in conjunction with administration of the composition, thereby suppressing a respiratory virus infection. The individual may have been exposed to or may be infected by a respiratory virus.

In another embodiment, the invention provides methods of reducing severity of a symptom of respiratory virus infection in an individual which entail administering an effective amount of a composition comprising a polynucleotide comprising an ISS to the individual, wherein the ISS comprises the sequence 5'-C, G-3' and wherein respiratory virus antigen is not administered in conjunction with administration of the composition, thereby reducing severity of a symptom of respiratory virus infection. The individual may be exposed to, at risk of exposure to, or infected by a respiratory virus.

In another embodiment, the invention provides methods of delaying development of a symptom of respiratory virus infection in an individual which entail administering effective amount of a composition comprising a polynucleotide comprising an ISS to the individual, wherein the ISS comprises the sequence 5'-C, G-3' and wherein respiratory virus antigen is not administered in conjunction with administration of the composition, thereby delaying development of a symptom of respiratory virus infection.

In another embodiment, the invention provides methods of reducing duration of a respiratory virus infection in an individual which entail administering effective amount of a composition comprising a polynucleotide comprising an ISS to the individual, wherein the ISS comprises the sequence 5'-C, G-3' and wherein respiratory virus antigen is not administered in conjunction with administration of the composition, thereby reducing duration of a respiratory virus infection. The individual may be exposed to, at risk of exposure to, or infected by a respiratory virus.

In further aspect, the invention provides kits for use in accordance with the methods of the invention. Accordingly, another embodiment of the invention provides kits for use in ameliorating and/or preventing a symptom of respiratory virus infection in an individual infected with, exposed to or at risk of being exposed to a respiratory virus. The kits comprise a composition comprising a polynucleotide comprising an ISS, wherein the ISS comprises the sequence 5'-C, G-3', wherein the kit does not comprise a respiratory virus antigen, and wherein the kits comprise instructions for administration of the composition to an individual infected with, exposed to or at risk of being exposed to a respiratory virus.

In some embodiments of the methods and kits of the invention, the ISS comprises the sequence 5'-purine, purine, C, G, pyrimidine, pyrimidine, C, G-3' or 5'-purine, purine, C, G, pyrimidine, pyrimidine, C, C-3'. In further embodiments of the methods and kits, the ISS comprises a sequence selected from the group consisting of AACGTTCC, AACGTTCG, GACGTTCC and GACGTTCG.

In some embodiments of the methods and kits of the invention, the ISS comprises the sequence 5'-T, C, G-3'. In some embodiments of the methods and kits of the invention, the ISS comprises the sequence 5'-TGACTGTGAACGTTC-GAGATGA-3' (SEQ ID NO:1).

In some embodiments of the methods and kits of the invention, the individual is a mammal. In further embodiments, the mammal is human.

In some embodiments of the methods and kits of the invention, the respiratory virus is respiratory syncytial virus (RSV). In other embodiments of the methods and kits of the invention, the respiratory virus is adenovirus. In other embodiments of the methods and kits of the invention, the respiratory virus is rhinovirus.

BRIEF DESCRIPTION OF THE DRAWINGS

FIG. 1 is a bar graph depicting lung RSV titer in rats which received intranasally: PBS (first bar); ISS three days before viral infection (second bar) non-ISS control sequence three days before viral infection (third bar); ISS 30 minutes before viral infection (fourth bar); non-ISS control sequence 30 minutes before viral infection.

MODES FOR CARRYING OUT THE INVENTION

We have discovered that immunostimulatory polynucleotide sequences (ISS) are effective anti-viral agents against respiratory viruses. A polynucleotide comprising an immunostimulatory sequence (an "ISS") is administered to an individual who is at risk of being exposed to respiratory virus, has been exposed to respiratory virus or is infected with respiratory virus. The ISS is administered without any respiratory virus antigens. Administration of the ISS without co-administration of a respiratory virus antigen results in reduced incidence and/or severity of one or more symptoms of respiratory virus infection.

The invention also relates to kits for ameliorating and/or preventing a symptom of respiratory virus infection in exposed individuals. The kits, which do not contain a respiratory virus antigen, comprise a polynucleotide comprising an ISS and instructions describing the administration of an ISS-containing polynucleotide to an individual for the intended treatment.

In an art-accepted model of a respiratory virus, namely cotton rat infected with respiratory syncytial virus (RSV), we have shown that ISS is effective at reducing viral titers especially if administered locally (i.e., at a site of infection) and at a sufficient time before viral infection. For example, rats pre-treated with an ISS non-locally (i.e., by IP injection) did not display significant reduction in viral titer although higher doses may have been efficacious. Further, there is no apparent toxicity at the therapeutic dosages (i.e., dosages sufficient to reduce viral titer). Significantly, in contrast to previous reports of immune modulation by ISS, we report clinical efficacy of ISS in this viral context.

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, *Molecular Cloning: A Laboratory Manual*, second edition (Sambrook et al., 1989); *Oligonucleotide Synthesis* (M. J. Gait, ed., 1984); *Animal Cell Culture* (R. I. Freshney, ed., 1987); *Methods in Enzymology* (Academic Press, Inc.); *Handbook of Experimental Immunology* (D. M. Weir & C. C. Blackwell, eds.); *Gene Transfer Vectors for Mammalian Cells* (J. M. Miller & M. P. Calos, eds., 1987); *Current Protocols in Molecular Biology* (F. M. Ausubel et al., eds., 1987); *PCR: The Polymerase Chain Reaction*, (Mullis et al., eds., 1994); *Current Protocols in Immunology* (J. E. Coligan et al., eds., 1991); *The Immunoassay Handbook* (David Wild, ed., Stockton Press NY, 1994); and *Methods of Immunological Analysis* (R. Masseyeff, W. H. Albert, and N. A. Staines, eds., Weinheim: VCH Verlags gesellschaft mbH, 1993).

DEFINITIONS

The term "respiratory virus" refers to a virus which infects cells of the respiratory tract, such as cells lining the oral cavity, nasopharynx, throat, larynx, bronchi and bronchioles, etc. Respiratory viruses include influenza virus, rhinovirus, adenovirus, respiratory syncytial virus (RSV), measles virus, mumps virus, parainfluenza virus, rubella virus, poxvirus, parvovirus, hantavirus and varicella virus. Statements and description which use the term "respiratory virus" indicate, and refer to, any one or more of the respiratory viruses listed herein.

"Exposure" to a virus denotes encounter with virus which allows infection, such as, for example, upon contact with an infected individual.

An individual is "seronegative" for a virus if antibodies specific to the virus cannot be detected in blood or serum samples from the individual using methods standard in the art, such as ELISA. Conversely, an individual is "seropositive" for a virus if antibodies specific for the virus can be detected in blood or serum samples from the individual using methods standard in the art, such as ELISA. An individual is said to "seroconvert" for a virus when antibodies to the virus can be detected in blood or serum from an individual who was previously seronegative.

An individual who is "at risk of being exposed" to a virus is an individual who may encounter the virus such that the virus infects the individual (i.e., virus enters cells and replicates). In the context of respiratory virus, which cause acute infection and resolution of infection and symptoms, the individual may or may not have previously been exposed to virus, but it is understood that, at the time of at least one administration of ISS-containing polynucleotide, the individual is symptom-free and has not been exposed to virus within about 5 days of administration of ISS. Because respiratory viruses are ubiquitous, generally any individual is at risk for exposure to the virus. In some contexts, an individual is determined to be "at risk" because exposure to the virus has higher probability of leading to infection (such as with immunocompromised, elderly and/or very young children and infants) which can further result in serious symptoms, conditions, and/or complications. In some settings, including, but not limited to, institutions such as hospitals, schools, day care facilities, military facilities, nursing homes and convalescent homes, an individual is determined to be "at risk" because of time spent in close proximity to others who may be infected.

"Suppressing" viral infection indicates any aspect of viral infection, such as viral replication, time course of infection, amount (titer) of virus, lesions, and/or one or more symptoms is curtailed, inhibited, or reduced (in terms of severity and/or duration) in an individual or a population of individuals treated with an ISS-containing polynucleotide in accordance with the invention as compared to an aspect of viral infection in an individual or a population of individuals not treated in accordance with the invention. Reduction in viral titer includes, but is not limited to, elimination of the virus from an infected site or individual. Viral infection can be assessed by any means known in the art, including, but not limited to, measurement of virus particles, viral nucleic acid or viral antigens, detection of symptoms and detection and/or measurement of anti-virus antibodies. Anti-virus antibodies are widely used to detect and monitor viral infection and generally are commercially available.

"Palliating" a disease or one or more symptoms of a disease or infection means lessening the extent and/or time course of undesirable clinical manifestations of a disease state or infection in an individual or population of individuals treated with an ISS in accordance with the invention.

As used herein, "delaying" development of a viral infection or a symptom of viral infection means to defer, hinder, slow, retard, stabilize, and/or postpone development of the disease or symptom when compared to not using the method(s) of the invention. This delay can be of varying lengths of time, depending on the history of the disease and/or individual being treated. As is evident to one skilled in the art, a sufficient or significant delay can, in effect, encompass prevention, in that the individual does not develop the disease.

"Reducing severity of a symptom" or "ameliorating a symptom" of viral infection means a lessening or improvement of one or more symptoms of viral infection as compared to not administering an ISS-containing polynucleotide. "Reducing severity" also includes shortening or reduction in duration of a symptom. For respiratory viruses, these symptoms are well known in the art and include, but are not limited to, inflammation of respiratory mucosa, fever, body aches, coughing, wheezing, sneezing, nasal discharge and chest pain.

"Preventing a symptom of infection" by a respiratory virus means that the symptom does not appear after exposure to the virus. Examples of symptoms have been described above.

"Reducing duration of viral infection" means the length of time of viral infection (usually indicated by symptoms) is reduced, or shortened, as compared to not administering an ISS-containing polynucleotide.

The term "infected individual", as used herein, refers to an individual who has been infected by a respiratory virus. Symptoms of respiratory virus infection are well known in the art and have been described herein.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom, and the progeny thereof. The definition also includes samples that have been manipulated in any way after their procurement, such as by treatment with reagents, solubilization, or enrichment for certain components, such as proteins or polynucleotides. The term "biological sample" encompasses a clinical sample, and also includes cells in culture, cell supernatants, cell lysates, serum, plasma, biological fluid, and tissue samples.

"Viral titer" is a term well known in the art and indicates the amount of virus in a given biological sample. "Viremia" is a term well-known in the art as the presence of virus in the blood stream and/or viral titer in a blood or serum sample. Amount of virus are indicated by various measurements, including, but not limited to, amount of viral nucleic acid; presence of viral particles; replicating units (RU); plaque forming units (PFU). Generally, for fluid samples such as blood and urine, amount of virus is determined per unit fluid, such as milliliters. For solid samples such as tissue samples, amount of virus is determined per weight unit, such as grams. Methods for determining amount of virus are known in the art and described herein.

An "individual" is a vertebrate, preferably a mammal, more preferably a human. Mammals include, but are not limited to, humans, farm animals, sport animals, rodents, primates and certain pets. Vertebrates also include, but are not limited to, birds (i.e., avian individuals) and reptiles (i.e., reptilian individuals).

The term "ISS" as used herein refers to polynucleotide sequences that effect a measurable immune response as measured in vitro, in vivo and/or ex vivo. Examples of measurable immune responses include, but are not limited to, antigen-specific antibody production, secretion of cytokines, activation or expansion of lymphocyte populations such as NK cells, $CD4^+$ T lymphocytes, $CD8^+$ T lymphocytes, B lymphocytes, and the like. Preferably, the ISS sequences preferentially activate a Th1-type response. A polynucleotide for use in methods of the invention contains at least one ISS.

As used interchangeably herein, the terms "polynucleotide" and "oligonucleotide" include single-stranded DNA (ssDNA), double-stranded DNA (dsDNA), single-stranded RNA (ssRNA) and double-stranded RNA (dsRNA), modified oligonucleotides and oligonucleosides or combinations thereof. The oligonucleotide can be linearly or circularly configured, or the oligonucleotide can contain both linear and circular segments.

"Adjuvant" refers to a substance which, when added to an immunogenic agent such as antigen, nonspecifically enhances or potentiates an immune response to the agent in the recipient host upon exposure to the mixture.

An "effective amount" or a "sufficient amount" of a substance is an amount sufficient to effect beneficial or desired results, including clinical results. An effective amount can be administered in one or more administrations. A "therapeutically effective amount" is an amount to effect beneficial clinical results, including, but not limited to, alleviation of one or more symptoms associated with viral infection as well as prevention of disease (e.g. prevention of one or more symptoms of infection).

A microcarrier is considered "biodegradable" if it is degradable or erodable under normal mammalian physiological conditions. Generally, a microcarrier is considered biodegradable if it is degraded (i.e., loses at least 5% of its mass or average and/or length) after a 72 hour incubation at 37° C. in normal human serum. Conversely, a microcarrier is considered "nonbiodegradable" if it is not degraded or eroded under normal mammalian physiological conditions. Generally, a microcarrier is considered nonbiodegradable if it not degraded (i.e., loses less than 5% of its mass and/or average polymer length) after at 72 hour incubation at 37° C. in normal human serum.

The term "immunostimulatory sequence-microcarrier complex" or "ISS-MC complex" refers to a complex of an ISS-containing polynucleotide and a microcarrier. The components of the complex may be covalently or non-covalently linked. Non-covalent linkages may be mediated by any non-covalent bonding force, including by hydrophobic interaction, ionic (electrostatic) bonding, hydrogen bonds and/or van der Waals attractions. In the case of hydrophobic linkages, the linkage is generally via a hydrophobic moiety (e.g., cholesterol) covalently linked to the ISS.

As used herein, the term "comprising" and its cognates are used in their inclusive sense; that is, equivalent to the term "including" and its corresponding cognates.

As used herein, the singular form "a", "an", and "the" includes plural references unless indicated otherwise. For example, "a" symptom of viral infection includes one or more additional symptoms.

METHODS OF THE INVENTION

The invention provides methods of ameliorating (i.e., reducing severity) and/or preventing symptoms of respiratory virus infection as well as methods of suppression of infection by a respiratory virus which entail administering an ISS-containing polynucleotide (used interchangeably herein with "ISS") to an individual without administering a respiratory virus antigen. An ISS-containing composition which does not include a respiratory virus antigen is administered to an individual at risk of exposure to, exposed to, infected with, and/or exhibiting symptoms of infection by a respiratory virus. Individuals receiving ISS are preferably mammal, more preferably human. In accordance with the invention, respiratory virus antigen is not administered to the individual in conjunction with administration of an ISS (i.e., is not administered in a separate administration at or about the time of administration of the ISS).

The respiratory virus may be any virus that infects the respiratory tract, including, but not limited to, influenza, respiratory syncytial virus (RSV), parainfluenza type 3 (PIV-3), adenovirus, rhinovirus, measles virus, mumps virus, other parainfluenza virus, rubella virus, poxvirus, parvovirus, hantavirus, varicella virus, paramyxovirus and myxovirus. In some embodiments, the respiratory virus is RSV. In some embodiments, the respiratory virus is other than influenza.

In some embodiments, the individual is at risk of being exposed to virus. Determination of an at risk individual is based on one or more factors that are associated with disease development and are generally known by, or can be assessed by, a skilled clinician. At risk individuals may be especially suitable candidates to receive ISS, as these individuals are generally considered to be particularly susceptible to developing symptoms of infection, which could also further lead to other complications. For example, in the context of RSV infection, age groups of about 2 years or less and the elderly would be considered at risk. Other individuals at risk include those that are in close proximity to individuals who may be infected including, but not limited to, health care workers, and individuals in institutions such as hospitals, schools, day care facilities, military facilities, nursing homes and convalescent homes. Other examples of at risk individuals are those who are immunocompromised.

In the context of influenza infection, generally the elderly (for example, aged 60 years and older) are considered at risk, although, as noted above, many other conditions put an individual at risk for this infection, such as during what is generally denoted "flu season" (November through March); conditions which involve significant contact with other people, such as family members of infected people and in office buildings, schools, airplanes, hospitals, schools, day care facilities, military facilities, nursing homes and convalescent homes. RSV season generally occurs during winter and early spring. The same general principles apply to the rhinovirus context.

In other embodiments, the individual is, or has been, exposed to and/or infected by virus. Exposure to virus is generally indicated by sufficient contact with an infected individual or infected location. Exposure can also be indicated by development of one or more symptoms associated with viral infection. Infection by virus may be indicated by any of the above, as well as detection of virus or anti-virus antibodies (i.e., the individual becomes seropositive) in a biological sample from the individual.

ISS

The methods of this invention entail administering a polynucleotide comprising an ISS (or a composition comprising such a polynucleotide). In accordance with the present invention, the immunomodulatory polynucleotide contains at least one ISS, and can contain multiple ISSs. The ISSs can be adjacent within the polynucleotide, or they can be separated by additional nucleotide bases within the polynucleotide. Alternately, multiple ISSs may be delivered as individual polynucleotides.

ISS have been described in the art and may be readily identified using standard assays which indicate various aspects of the immune response, such as cytokine secretion, antibody production, NK cell activation and T cell proliferation. See, e.g., WO 97/28259; WO 98/16247; WO 99/11275; Krieg et al. (1995); Yamamoto et al. (1992); Ballas et al. (1996); Klinman et al. (1997); Sato et al. (1996); Pisetsky (1996a); Shimada et al. (1986) *Jpn. J. Cancer Res.* 77:808-816; Cowdery et al. (1996) *J. Immunol.* 156:4570-457-5; Roman et al. (1997); and Lipford et al. (1997a).

The ISS can be of any length greater than 6 bases or base pairs and generally comprises the sequence 5'-cytosine, guanine-3', preferably greater than 15 bases or base pairs, more preferably greater than 20 bases or base pairs in length. As is well-known in the art, the cytosine of the 5'-cytosine, guanine-3' sequence is unmethylated. An ISS may also comprise the sequence 5'-purine, purine, C, G, pyrimidine, pyrimidine, C, G-3'. An ISS may also comprise the sequence 5'-purine, purine, C, G, pyrimidine, pyrimidine, C, C-3'. As indicated in polynucleotide sequences below, an ISS may comprise (i.e., contain one or more of) the sequence 5'-T, C, G-3'. In some embodiments, an ISS may comprise the sequence 5'-C, G, pyrimidine, pyrimidine, C, G-3' (such as 5'-CGTTCG-3'). In some embodiments, an ISS may comprise the sequence 5'-C, G, pyrimidine, pyrimidine, C, G, purine, purine-3'. In some embodiments, an ISS comprises the sequence 5'-purine, purine, C, G, pyrimidine, pyrimidine-3' (such as 5'-AACGTT-3').

In some embodiments, an ISS may comprise the sequence 5'-purine, T, C, G, pyrimidine, pyrimidine-3'.

In some embodiments, an ISS-containing polynucleotide is less than about any of the following lengths (in bases or base pairs): 10,000; 5,000; 2500; 2000; 1500; 1250; 1000; 750; 500; 300; 250; 200; 175; 150; 125; 100; 75; 50; 25; 10. In some embodiments, an ISS-containing polynucleotide is greater than about any of the following lengths (in bases or base pairs): 8; 10; 15; 20; 25; 30; 40; 50; 60; 75; 100; 125; 150; 175; 200; 250; 300; 350; 400; 500; 750; 1000; 2000; 5000; 7500; 10000; 20000; 50000. Alternately, the ISS can be any of a range of sizes having an upper limit of 10,000; 5,000; 2500; 2000; 1500; 1250; 1000; 750; 500; 300; 250; 200; 175; 150; 125; 100; 75; 50; 25; or 10 and an independently selected lower limit of 8; 10; 15; 20; 25; 30; 40; 50; 60; 75; 100; 125; 150; 175; 200; 250; 300; 350; 400; 500; 750; 1000; 2000; 5000; 7500, wherein the lower limit is less than the upper limit.

In some embodiments, the ISS comprises any of the following sequences:

GACGCTCC; GACGTCCC; GACGTTCC; GACGCCC; AGCGTTCC;

AGCGCTCC; AGCGTCCC; AGCGCCCC; AACGTCCC; AACGCCCC;

AACGTTCC; AACGCTCC; GGCGTTCC; GGCGCTCC; GGCGTCCC;

GGCGCCCC; GACGCTCG; GACGTCCG; GACGCCCG; GACGTTCG;

AGCGCTCG; AGCGTTCG; AGCGTCCG; AGCGCCCG; AACGTCCG;

AACGCCCG; AACCTTCG; AACGCTCG; GGCGTTCG; GGCGCTCG;

GGCGTCCG; GGCGCCCG.

In some embodiments, the immunomodulatory polynucleotide comprises the sequence 5'-TGACTGTGAACGTTC-GAGATGA-3' (SEQ ID NO:1).

In some embodiments, the ISS comprises any of the following sequences:

GACGCU; GACGUC; GACGUU; GACGUT; GACGTU; AGCGUU;

AGCGCU; AGCGUC; AGCGUT; AGCGTU; AACGUC; AACGUU;

AACGCU; AACGUT; AACGTU; GGCGUU; GGCGCU; GGCGUC;

GGCGUT; GGCGTU.

In some embodiments, the ISS comprises any of the following sequences:

GABGCTCC; GABGTCCC; GABGTTCC; GABGCCCC; AGBGTTCC;

AGBGCTCC; AGBGTCCC; AGBGCCCC; AABGTCCC; AABGCCCC;

AABGTTCC; AABGCTCC; GGBGTTCC; GGBGCTCC; GGBGTCCC;

GGBGCCCC; GABGCTCG; GABGTCCG; GABGCCCG; GABGTTCG;

AGBGCTCG; AGBGTTCG; AGBGTCCG; AGBGCCCG; AABGTCCG;

AABGCCCG; AABGTTCG; AABGCTCG; GGBGTTCG; GGBGCTCG;

GGBGTCCG; GGBGCCCG; GABGCTBG; GABGTCBG; GABGCCBG;

GABGTTBG; AGBGCTBG; AGBGTTBG; AGBGTCBG; AGBGCCBG;

AABGTCBG; AABGCCBG; AABGTTBG; AABGCTBG; GGBGTTBG;

GGBGCTBG; GGBGTCBG; GGBGCCBG, where B is 5-bromocytosine.

In some embodiments, the ISS comprises any of the following sequences:

GABGCUCC; GABGUCCC; GABGUTCC; GABGTUCC; GABGUUCC;

AGBGUUCC; AGBGTUCC; AGBGUTCC; AGBGCUCC; AGBGUCCC;

AABGUCCC; AABGUUCC; AABGUTCC; AABGTUCC; AABGCUCC;

GGBGUUCC; GGBGUTCC; GGBGTUCC; GGBGCUCC; GGBGUCCC;

GABGCUCG; GABGUCCG; GABGUUCG; GABGUTCG; GABGTUCG;

AGBGCUCG; AGBGUUCG; AGBGUTCG; AGBGTUCG; AGBGUCCG;

AABGUCCG; AABGUUCG; AABGUTCG; AABGTUCG; AABGCUCG;

GGBGUUCG; GGBGUTCG; GGBGTUCG; GGBGCUCG; GGBGUCCG;

GABGCUBG; GABGUCBG; GABGUUBG; GABGUTBG; GABGTUBG;

AGBGCUBG; AGBGUUBG; AGBGUCBG; AGBGUTBG; AGBGTUBG;

AABGUCBG; AABGUUBG; AABGUTBG; AABGTUBG; AABGCUBG;

GGBGUUBG; GGBGUTBG; GGBGTUBG; GGBGCUBG; GGBGUCBG, where B is 5-bromocytosine.

In other embodiments, the ISS comprises any of the sequences:

5'-TGACCGTGAACGTTCGAGATGA-3'; (SEQ ID NO: 2)

5'-TCATCTCGAACGTTCCACAGTCA-3'; (SEQ ID NO: 3)

5'-TGACTGTGAACGTTCCAGATGA-3'; (SEQ ID NO: 4)

5'-TCCATAACGTTCGCCTAACGTTCGTC-3'; (SEQ ID NO: 5)

5'-TGACTGTGAABGTTCCAGATGA-3', (SEQ ID NO: 6)

where B is 5-bromocytosine;
5'-TGACTGTGAABGTTCGAGATGA-3' (SEQ ID NO:7), where B is 5-bromocytosine and
5'-TGACTGTGAABGTTBGAGATGA-3' (SEQ ID NO:8), where B is 5-bromocytosine.

An ISS and/or ISS-containing polynucleotide may contain modifications. Modifications of ISS include any known in the art, but are not limited to, modifications of the 3'-OH or 5'-OH group, modifications of the nucleotide base, modifications of the sugar component, and modifications of the phosphate group. Various such modifications are described below.

An ISS may be single stranded or double stranded DNA, as well as single or double-stranded RNA or other modified polynucleotides. An ISS may or may not include one or more palindromic regions, which may be present in the motifs described above or may extend beyond the motif. An ISS may comprise additional flanking sequences, some of which are described herein. An ISS may contain naturally-occurring or modified, non-naturally occurring bases, and may contain modified sugar, phosphate, and/or termini. For example, phosphate modifications include, but are not limited to, methyl phosphonate, phosphorothioate, phosphoramidate (bridging or non-bridging), phosphotriester and phosphorodithioate and may be used in any combination. Other non-phosphate linkages may also be used. Preferably, oligonucleotides of the present invention comprise phosphorothioate backbones. Sugar modifications known in the field, such as 2'-alkoxy-RNA analogs, 2'-amino-RNA analogs and 2'-alkoxy- or amino-RNA/DNA chimeras and others described herein, may also be made and combined with any phosphate modification. Examples of base modifications include, but are not limited to, addition of an electron-withdrawing moiety to C-5 and/or C-6 of a cytosine of the ISS (e.g., 5-bromocytosine, 5-chlorocytosine, 5-fluorocytosine, 5-iodocytosine).

The ISS can be synthesized using techniques and nucleic acid synthesis equipment which are well known in the art including, but not limited to, enzymatic methods, chemical methods, and the degradation of larger oligonucleotide sequences. See, for example, Ausubel et al. (1987); and Sambrook et al. (1989). When assembled enzymatically, the individual units can be ligated, for example, with a ligase such as T4 DNA or RNA ligase. U.S. Pat. No. 5,124,246. Oligonucleotide degradation can be accomplished through the exposure of an oligonucleotide to a nuclease, as exemplified in U.S. Pat. No. 4,650,675.

The ISS can also be isolated using conventional polynucleotide isolation procedures. Such procedures include, but are not limited to, hybridization of probes to genomic or cDNA libraries to detect shared nucleotide sequences, antibody screening of expression libraries to detect shared structural features and synthesis of particular native sequences by the polymerase chain reaction.

Circular ISS can be isolated, synthesized through recombinant methods, or chemically synthesized. Where the circular ISS is obtained through isolation or through recombinant methods, the ISS will preferably be a plasmid. The chemical synthesis of smaller circular oligonucleotides can be performed using any method described in the literature. See, for instance, Gao et al. (1995) *Nucleic Acids Res.* 23:2025-2029; and Wang et al. (1994) *Nucleic Acids Res.* 22:2326-2333.

The techniques for making oligonucleotides and modified oligonucleotides are known in the art. Naturally occurring DNA or RNA, containing phosphodiester linkages, is generally synthesized by sequentially coupling the appropriate nucleoside phosphoramidite to the 5'-hydroxy group of the growing oligonucleotide attached to a solid support at the 3'-end, followed by oxidation of the intermediate phosphite triester to a phosphate triester. Once the desired oligonucleotide sequence has been synthesized, the oligonucleotide is removed from the support, the phosphate triester groups are deprotected to phosphate diesters and the nucleoside bases are deprotected using aqueous ammonia or other bases. See, for example, Beaucage (1993) "Oligodeoxyribonucleotide Synthesis" in *Protocols for Oligonucleotides and Analogs, Synthesis and Properties* (Agrawal, ed.) Humana Press, Totowa, N.J.; Warner et al. (1984) *DNA* 3:401 and U.S. Pat. No. 4,458,066.

The ISS can also contain phosphate-modified oligonucleotides. Synthesis of polynucleotides containing modified phosphate linkages or non-phosphate linkages is also know in the art. For a review, see Matteucci (1997) "Oligonucleotide Analogs: an Overview" in *Oligonucleotides as Therapeutic Agents*, (D. J. Chadwick and G. Cardew, ed.) John Wiley and Sons, New York, N.Y. The phosphorous derivative (or modified phosphate group) which can be attached to the sugar or sugar analog moiety in the oligonucleotides of the present invention can be a monophosphate, diphosphate, triphosphate, alkylphosphonate, phosphorothioate, phosphorodithioate or the like. The preparation of the above-noted phosphate analogs, and their incorporation into nucleotides, modified nucleotides and oligonucleotides, per se, is also known and need not be described here in detail. Peyrottes et al. (1996) *Nucleic Acids Res.* 24:1841-1848; Chaturvedi et al. (1996) *Nucleic Acids Res.* 24:2318-2323; and Schultz et al. (1996) *Nucleic Acids Res.* 24:2966-2973. For example, synthesis of phosphorothioate oligonucleotides is similar to that described above for naturally occurring oligonucleotides except that the oxidation step is replaced by a sulfurization step (Zon (1993) "Oligonucleoside Phosphorothioates" in *Protocols for Oligonucleotides and Analogs, Synthesis and Properties* (Agrawal, ed.) Humana Press, pp. 165-190). Similarly the synthesis of other phosphate analogs, such as phosphotriester (Miller et al. (1971) *JACS* 93:6657-6665), non-bridging phosphoramidates (Jager et al. (1988) *Biochem.* 27:7247-7246), N3' to P5' phosphoramidates (Nelson et al. (1997) *JOC* 62:7278-7287) and phosphorodithioates (U.S. Pat. No. 5,453,496) has also been described. Other non-phosphorous based modified oligonucleotides can also be used (Stirchak et al. (1989) *Nucleic Acids Res.* 17:6129-6141). Oligonucleotides with phosphorothioate backbones can be more immunogenic than those with phosphodiester backbones and appear to be more resistant to degradation after injection into the host. Braun et al. (1988) *J. Immunol.* 141: 2084-2089; and Latimer et al. (1995) *Mol. Immunol.* 32:1057-1064.

ISS-containing polynucleotides used in the invention can comprise ribonucleotides (containing ribose as the only or principal sugar component), deoxyribonucleotides (containing deoxyribose as the principal sugar component), or, as is known in the art, modified sugars or sugar analogs can be incorporated in the ISS. Thus, in addition to ribose and deoxyribose, the sugar moiety can be pentose, deoxypentose, hexose, deoxyhexose, glucose, arabinose, xylose, lyxose, and a sugar "analog" cyclopentyl group. The sugar can be in pyranosyl or in a furanosyl form. In the ISS, the sugar moiety is preferably the furanoside of ribose, deoxyribose, arabinose or 2'-0-alkylribose, and the sugar can be attached to the respective heterocyclic bases either in α or β anomeric configuration. Sugar modifications include, but are not limited to, 2'-alkoxy-RNA analogs, 2'-amino-RNA analogs and 2'-alkoxy- or amino-RNA/DNA chimeras. The preparation of these sugars or sugar analogs and the respective "nucleosides" wherein such sugars or analogs are attached to a heterocyclic base (nucleic acid base) per se is known, and need not be described here, except to the extent such preparation can pertain to any specific example. Sugar modifications may also be made and combined with any phosphate modification in the preparation of an ISS.

The heterocyclic bases, or nucleic acid bases, which are incorporated in the ISS can be the naturally-occurring principal purine and pyrimidine bases, (namely uracil or thymine, cytosine, adenine and guanine, as mentioned above), as well as naturally-occurring and synthetic modifications of said principal bases.

Those skilled in the art will recognize that a large number of "synthetic" non-natural nucleosides comprising various heterocyclic bases and various sugar moieties (and sugar analogs) are available in the art, and that as long as other criteria of the present invention are satisfied, the ISS can include one or several heterocyclic bases other than the principal five base components of naturally-occurring nucleic acids. Preferably, however, the heterocyclic base in the ISS includes, but is not limited to, uracil-5-yl, cytosin-5-yl, adenin-7-yl, adenin-8-yl, guanin-7-yl, guanin-8-yl, 4-aminopyrrolo[2,3-d]pyrimidin-5-yl, 2-amino-4-oxopyrolo[2,3-d]pyrimidin-5-yl, 2-amino-4-oxopyrrolo[2,3-d]pyrimidin-3-yl groups, where the purines are attached to the sugar moiety of the ISS via the 9-position, the pyrimidines via the 1-position, the pyrrolopyrimidines via the 7-position and the pyrazolopyrimidines via the 1-position.

The ISS may comprise at least one modified base as described, for example, in the commonly owned international application WO 99/62923. As used herein, the term "modified base" is synonymous with "base analog", for example, "modified cytosine" is synonymous with "cytosine analog." Similarly, "modified" nucleosides or nucleotides are herein defined as being synonymous with nucleoside or nucleotide "analogs." Examples of base modifications include, but are not limited to, addition of an electron-withdrawing moiety to C-5 and/or C-6 of a cytosine of the ISS. Preferably, the electron-withdrawing moiety is a halogen. Such modified cytosines can include, but are not limited to, azacytosine, 5-bromocytosine, bromouracil, 5-chlorocytosine, chlorinated cytosine, cyclocytosine, cytosine arabinoside, 5-fluorocytosine, fluoropyrimidine, fluorouracil, 5,6-dihydrocytosine, 5-iodocytosine, hydroxyurea, iodouracil, 5-nitrocytosine, uracil, and any other pyrimidine analog or modified pyrimidine.

The preparation of base-modified nucleosides, and the synthesis of modified oligonucleotides using said base-modified nucleosides as precursors, has been described, for example, in U.S. Pat. Nos. 4,910,300, 4,948,882, and 5,093,232. These base-modified nucleosides have been designed so that they can be incorporated by chemical synthesis into either terminal or internal positions of an oligonucleotide. Such base-modified nucleosides, present at either terminal or internal positions of an oligonucleotide, can serve as sites for attachment of a peptide or other antigen. Nucleosides modified in their sugar moiety have also been described (including, but not limited to, e.g., U.S. Pat. Nos. 4,849,513, 5,015,733, 5,118,800, 5,118,802) and can be used similarly.

The ISS used in the methods of the invention may be produced as ISS-microcarrier complexes. ISS-microcarrier complexes comprise an ISS-containing polynucleotide bound to a microcarrier (MC). ISS-MC complexes comprise an ISS bound to the surface of a microcarrier (i.e., the ISS is not encapsulated in the MC), adsorbed within a microcarrier (e.g., adsorbed to PLGA beads), or encapsulated within a MC (e.g., incorporated within liposomes).

ISS-containing oligonucleotides bound to microparticles (SEPHAROSE® beads) have previously been shown to have immunostimulatory activity in vitro (Liang et al., (1996), *J. Clin. Invest.* 98:1119-1129). However, recent results show that ISS-containing oligonucleotides bound to gold, latex and magnetic particles are not active in stimulating proliferation of 7TD1 cells, which proliferate in response to ISS-containing oligonucleotides (Manzel et al., (1999), *Antisense Nucl. Acid Drug Dev.* 9:459-464).

Microcarriers are not soluble in pure water, and are less than about 50-60 µm in size, preferably less than about 10 µm in size, more preferably from about 10 nm to about 10 µm, 25 nm to about 5 µm, 50 nm to about 4.5 µm or 1.0 µm to about 2.0 µm in size. Microcarrers may be any shape, such as spherical, ellipsoidal, rod-shaped, and the like, although spherical microcarriers are normally preferred. Preferred microcarriers have sizes of or about 50 nm, 200 nm, 1 µm, 1.2 µm, 1.4 µm, 1.5 µm, 1.6 µm, 1.8 µm, 2.0 µm, 2.5 µm or 4.5 µm. The "size" of a microcarrier is generally the "design size" or intended size of the particles stated by the manufacturer. Size may be a directly measured dimension, such as average or maximum diameter, or may be determined by an indirect assay such as a filtration screening assay. Direct measurement of microcarrier size is typically carried out by microscopy, generally light microscopy or scanning electron microscopy (SEM), in comparison with particles of known size or by reference to a micrometer. As minor variations in size arise during the manufacturing process, microcarriers are considered to be of a stated size if measurements show the microcarriers are ± about 5-10% of the stated measurement. Size characteristics may also be determined by dynamic light scattering. Alternately, microcarrier size may be determined by filtration screening assays. A microcarrier is less than a stated size if at least 97% of the particles pass through a "screen-type" filter (i.e., a filter in which retained particles are on the surface of the filter, such as polycarbonate or polyethersulfone filters, as opposed to a "depth filter" in which retained particles lodge within the filter) of the stated size. A microcarrier is larger than a stated size if at least about 97% of the microcarrier particles are retained by a screen-type filter of the stated size. Thus, at least about 97% microcarriers of about 10 µm to about 10 nm in size pass through a 10 µm pore screen filter and are retained by a 10 nm screen filter.

As above discussion indicates, reference to a size or size range for a microcarrier implicitly includes approximate variations and approximations of the stated size and/or size range. This is reflected by use of the term "about" when referring to a size and/or size range, and reference to a size or size range without reference to "about" does not mean that the size and/or size range is exact.

Microcarriers may be solid phase (e.g., polystyrene beads) or liquid phase (e.g., liposomes, micelles, or oil droplets in an oil and water emulsion). Liquid phase microcarriers include liposomes, micelles, oil droplets and other lipid or oil-based particles. One preferred liquid phase microcarrier is oil droplets within an oil-in-water emulsion. Preferably, oil-in-water emulsions used as microcarriers comprise biocompatible substituents such as squalene. Liquid phase microcarriers are normally considered nonbiodegradable, but may be biodegradable liquid phase microcarriers may be produced by incorporation of one or more biodegradable polymers in the liquid microcarrier formulation. In one preferred, embodiment, the microcarrier is oil droplets in an oil-in-water emulsion prepared by emulsification of squalene, sorbitan trioleate, TWEEN 80® in an aqueous pH buffer.

Solid phase microcarriers for use in ISS-microcarrier complexes may be made from biodegradable materials or nonbiodegradable materials, and may include or exclude agarose or modified agarose microcarriers. Useful solid phase biodegradable microcarriers include, but are not limited to: biodegradable polyesters, such as poly(lactic acid), poly(glycolic acid), and copolymers (including block copolymers) thereof, as well as block copolymers of poly(lactic acid) and poly(ethylene glycol); polyorthoesters such as polymers based on 3,9-diethylidene-2,4,8,10-tetraoxaspiro[5.5]undecane (DETOSU); polyanhydrides such as poly(anhydride) polymers based on sebacic acid, p-(carboxyphenoxy)propane, or p-(carboxyphenoxy)hexane; polyanhydride imides, such as polyanhydride polymers based on sebacic acid-derived monomers incorporating amino acids (i.e., linked to sebacic acid by imide bonds through the amino-terminal nitrogen) such as glycine or alanine; polyanhydride esters; polyphosphazenes, especially poly(phosphazenes) which contain hydrolysis-sensitive ester groups which can catalyze degradation of the polymer backbone through generation of carboxylic acid groups (Schacht et al. (1996) *Biotechnol. Bioeng.* 1996:102); and polyamides such as poly(lactic acid-co-lysine). A wide variety of nonbiodegradable materials suitable for manufacturing microcarriers are also known, including, but not limited to polystyrene, polyethylene, latex, gold, and ferromagnetic or paramagnetic materials. Solid phase microcarriers may be covalently modified to incorporate one or more moieties for use in linking the ISS, for example by addition of amine groups for covalent linking using amine-reactive crosslinkers.

The ISS-microcarrier complexes of the invention may be covalently or non-covalently linked. Covalently linked ISS-MC complexes may be directly linked or be linked by a crosslinking moiety of one or more atoms (typically the residue of a crosslinking agent). The ISS may be modified to allow or augment binding to the MC (e.g., by incorporation of a free sulfhydryl for covalent crosslinking or addition of a hydrophobic moieties such as lipids, steroids, sterols such as cholesterol, and terpenes, for hydrophobic bonding), although unmodified ISS may be used for formation of non-covalent ISS-MC complex formation by electrostatic interaction or by base pairing (e.g., by base pairing at least one portion of the ISS with a complementary oligonucleotide bound to the microcarrier). ISS-containing polynucleotides may be linked to solid phase microcarriers or other chemical moieties to facilitate ISS-MC complex formation using conventional technology known in the art, such as use of available heterobifunctional crosslinkers (e.g., succinimidyl 4-(N-maleimidomethyl)cyclohexane-1-carboxylate or its sulfo-derivatives for covalently linking an amine-derivatized microcarrier and an ISS modified to contain a free sulfhydryl) or by addition of compounds such as cholesterol (e.g., by the method of Godard et al. (1995) *Eur. J. Biochem.* 232:404-410) to facilitate binding to hydrophobic microcarriers such as oil droplets in oil-in-water emulsions. Alternatively, modified nucleosides or nucleotides, such as are known in the art, can be incorporated at either terminus, or at internal positions in the ISS. These can contain blocked functional groups which, when deblocked, are reactive with a variety of functional groups which can be present on, or attached to, the microcarrier or a moiety which would facilitate binding to a microcarrier. Certain embodiments of noncovalently linked ISS-MC complexes utilize a binding pair (e.g., an antibody and its cognate antigen or biotin and streptavidin or avidin), where one member of the binding pair is bound to the ISS and the microcarrier is derivatized with the other member of the binding pair (e.g., a biotinylated ISS and a streptavidin-derivatized microcarrier may be combined to form a noncovalently linked ISS-MC complex).

Non-covalent ISS-MC complexes bound by electrostatic binding typically exploit the highly negative charge of the polynucleotide backbone. Accordingly, microcarriers for use in non-covalently bound ISS-MC complexes are generally positively charged at physiological pH (e.g., about pH 6.8-7.4). The microcarrier may intrinsically possess a positive charge, but microcarriers made from compounds not normally possessing a positive charge may be derivatized or otherwise modified to become positively charged. For example, the polymer used to make the microcarrier may be derivatized to add positively charged groups, such as primary amines. Alternately, positively charged compounds may be incorporated in the formulation of the microcarrier during manufacture (e.g., positively charged surfactants may be used during the manufacture of poly(lactic acid)/poly(glycolic acid) copolymers to confer a positive charge on the resulting microcarrier particles.

Solid phase microspheres are prepared using techniques known in the art. For example, they can be prepared by emulsion-solvent extraction/evaporation technique. Generally, in this technique, biodegradable polymers such as polyanhydrates, poly(alkyl-α-cyanoacrylates) and poly(α-hydroxy esters), for example, poly(lactic acid), poly(glycolic acid), poly(D,L-lactic-co-glycolic acid) and poly(caprolactone), are dissolved in a suitable organic solvent, such as methylene chloride, to constitute the dispersed phase (DP) of emulsion. DP is emulsified by high-speed homogenization into excess volume of aqueous continuous phase (CP) that contains a dissolved surfactant, for example, polyvinylalcohol (PVA) or polyvinylpirrolidone (PVP). Surfactant in CP is to ensure the formation of discrete and suitably-sized emulsion droplet. The organic solvent is then extracted into the CP and subsequently evaporated by raising the system temperature. The solid microparticles are then separated by centrifugation or filtration, and dried, for example, by lyophilization or application of vacuum, before storing at 4° C.

Generally, to prepare cationic microspheres, cationic lipids or polymers, for example, 1,2-dioleoyl-1,2,3-trimethylammoniopropane (DOTAP), cetyltrimethylammonium bromide (CTAB) or polylysine, are added either to DP or CP, as per their solubility in these phases.

Physico-chemical characteristics such as mean size, size distribution and surface charge of dried microspheres may be determined. Size characteristics are determined, for example, by dynamic light scattering technique and the surface charge was determined by measuring the zeta potential.

Generally, ISS-containing polynucleotides can be adsorbed onto the cationic microspheres by overnight aqueous incubation of ISS and the particles at 4° C. Microspheres are characterized for size and surface charge before and after ISS association. Selected batches may then evaluated for activity as described herein.

Administration

An ISS-containing polynucleotide may be administered before, during and/or after exposure to a respiratory virus. An ISS polynucleotide may also be administered before, during and/or after infection by a respiratory virus. An ISS polynucleotide may also be administered before or after onset of symptoms of respiratory virus infection. Accordingly, administration of ISS-containing polynucleotide may be at various times with respect to exposure to, infection by and/or onset of symptoms by infection by virus. Further, there may be one or more administrations. If the ISS-containing polynucleotide is administered on multiple occasions, the ISS may be administered on any schedule selected by the clinician, such as daily, every other day, every three days, every four days, every five days, every six days, weekly, biweekly, monthly or at ever longer intervals (which may or may not remain the same during the course of treatment). Where multiple administrations are given, the ISS-containing polynucleotide may be given in 2, 3, 4, 5, 6, 7, 8, 9, 10 or more separate administrations. Generally, but not necessarily, an interval of at least about three days is necessary to allow effect of ISS-containing polynucleotides.

When ISS-containing polynucleotide is administered to an individual at risk of exposure to virus (i.e., before infection), ISS-containing polynucleotide is preferably administered less than about 14 days before exposure to virus, preferably less than about 10 days before exposure to virus, more preferably less than about 7 days before exposure to virus, even more preferably less than about 5 days before exposure to virus. In some embodiments, ISS-containing polynucleotide is administered about 3 days before exposure to virus.

In a further embodiment, the ISS-containing polynucleotide is administered after exposure to a respiratory virus, but prior to appearance of symptoms. Preferably, the ISS-containing polynucleotide is administered less than about three days after exposure, more preferably less than about one day, 12 hours, six hours or two hours after exposure, if the time of exposure is known or suspected.

In another embodiment, the ISS-containing polynucleotide is administered after appearance of at least one symptom of respiratory virus infection. Preferably, ISS-containing polynucleotide is administered within about 28, 21, 14, 7, 5 or 3 days following appearance of a symptom of respiratory virus infection. However, some infected individuals exhibiting symptoms will already have undertaken one or more courses of treatment with another therapy. In such individuals, or in individuals who failed to appreciate the import of their symptoms, the ISS-containing polynucleotide may be administered at any point following infection.

Additionally, treatments employing an ISS-containing polynucleotide may also be employed in conjunction with other treatments or as 'second line' treatments employed after failure of a 'first line' treatment. Treatments for respiratory virus infection are known in the art.

ISS polynucleotides may be formulated in any form known in the art, such as dry powder, semi-solid or liquid formulations. For parenteral administration ISS polynucleotides preferably administered in a liquid formulation, although solid or semi-solid formulations may also be acceptable, particularly where the ISS polynucleotide is formulated in a slow release depot form. ISS polynucleotides are generally formulated in liquid or dry powder form for topical administration, although semi-solid formulations may occasionally be useful.

ISS polynucleotide formulations may contain additional components such as salts, buffers, bulking agents, osmolytes, antioxidants, detergents, surfactants and other pharmaceutically-acceptable excipients as are known in the art. Generally, liquid ISS polynucleotide formulations made in USP water for injection and are sterile, isotonic and pH buffered to a physiologically-acceptable pH, such as about pH 6.8 to 7.5.

ISS-containing polynucleotides may be formulated in delivery vehicles such as liposomes, oil/water emulsion or slow release depot formulations. Methods of formulating polynucleotides in such forms are well known in the art.

ISS-containing polynucleotide formulations may also include or exclude immunomodulatory agents such as adjuvants and immunostimulatory cytokines, which are well known in the art.

A suitable dosage range or effective amount is one that provides the desired reduction of symptoms and/or suppression of viral infection and depends on a number of factors, including the particular respiratory virus, ISS sequence of the polynucleotide, molecular weight of the polynucleotide and route of administration. Dosages are generally selected by the physician or other health care professional in accordance with a variety of parameters known in the art, such as severity of symptoms, history of the patient and the like. Generally, for an ISS-containing polynucleotide of about 20 bases, a dosage range may be selected from, for example, an independently selected lower limit such as about 0.1, 0.25, 0.5, 1, 2, 5, 10, 20, 30, 40, 50, 60, 80, 100, 200, 300, 400 or 500 µg/kg up to an independently selected upper limit, greater than the lower limit, of about 60, 80, 100, 200, 300, 400, 500, 750, 1000, 1500, 2000, 3000, 4000, 5000, 6000, 7000, 8000, 9000 or 10,000 µg/kg. For example, a dose may be about any of the following: 0.1 to 100 µg/kg, 0.1 to 50 µg/kg, 0.1 to 25 µg/kg, 0.1 to 10 µg/kg, 1 to 500 µg/kg, 100 to 400 µg/kg, 200 to 300 µg/kg, 1 to 100 µg/kg, 100 to 200 µg/kg, 300 to 400 µg/kg, 400 to 500 µg/kg, 500 to 1000 µg/kg, 500 to 5000 µg/kg, or 500 to 10,000 µg/kg. Generally, parenteral routes of administration may require higher doses of ISS compared to more direct application to infected tissue, as do ISS-containing polynucleotides of increasing length.

Polynucleotides comprising an ISS may be administered by systemic (e.g., parenteral) or local (e.g., topical) administration.

In one embodiment, the ISS-containing polynucleotide(s) is topically administered, at a site of infection, such as respiratory mucosa (such as nasal passages or lung). Nasopharyngeal and pulmonary routes of administration include, but are not limited to, intranasal, inhalation, transbronchial and transalveolar routes. The ISS-containing polynucleotide may thus be administered by inhalation of aerosols, atomized liquids or powders. Devices suitable for administration by inhalation of ISS-containing compositions include, but are not limited to, nebulizers, atomizers, vaporizers, and metered-dose inhalers. Nebulizers, atomizers, vaporizers and metered-dose inhalers filled with or employing reservoirs containing formulations comprising the ISS-containing polynucleotide(s) are among a variety of devices suitable for use in inhalation delivery of the ISS-containing polynucleotide(s). Other methods of delivering to respiratory mucosa include delivery of liquid formulations, such as by nose drops.

In other embodiments, the ISS-containing polynucleotide is administered parenterally. Parenteral routes of administration include, but are not limited to, transdermal, transmucosal and direct injection. Parenteral administration by injection may be by any parenteral injection route, including, but not limited to, intravenous (IV), intraperitoneal (IP), intramuscular (IM), subcutaneous (SC) and intradermal (ID) routes. Transdermal and transmucosal administration may be accomplished by, for example, inclusion of a carrier (e.g., dimethylsulfoxide, DMSO), by application of electrical impulses (e.g., iontophoresis) or a combination thereof. A variety of devices are available for transdermal administration which may be used in accordance with the invention.

Because respiratory viruses infect cells of the respiratory tract, routes which deliver ISS polynucleotides to the respiratory tract, such as inhalation and intranasal delivery (discussed above), are considered local routes of administration rather than systemic routes of administration, even though delivery through such routes are normally considered parenteral, systemic routes of administration.

IV, IP, IM and ID administration may be by bolus or infusion administration. For SC administration, administration may be by bolus, infusion or by implantable device, such as an implantable minipump (e.g., osmotic or mechanical minipump) or slow release implant. The ISS polynucleotide(s) may also be delivered in a slow release formulation adapted for IV, IP, IM, ID or SC administration. Administration by inhalation is preferably accomplished in discrete doses (e.g., via a metered dose inhaler), although delivery similar to an infusion may be accomplished through use of a nebulizer. Administration via the transdermal and transmucosal routes may be continuous or pulsatile.

Respiratory Syncytial Virus (RSV)

If the respiratory virus is RSV, administration (at least a first administration) preferably occurs less than about 10 days, preferably less than about 7 days, preferably about 3 days prior to exposure to virus. Even more preferably, administration(s) is local, such as aerosol administration to nasal and/or bronchial passages. The ISS containing polynucleotide may comprise the sequence 5'-T, C, G-3'. The ISS containing polynucleotide used preferably comprises the sequence 5'-purine, purine, C, G, pyrimidine, pyrimidine C, G-3', more preferably comprises 5'-AACGTTCG-3', and more preferably comprises (or, alternatively, consists of) the sequence 5'-TGACTGTGAACGTTCGAGATGA-3' (SEQ ID NO: 1).

Assessment

In some embodiments, administration of an ISS-containing polynucleotide results in prevention, palliation, and/or improvement in one or more symptoms of respiratory virus infection, such as RSV infection. The exact form of prevention, palliation or improvement will depend on the particular respiratory virus. In some embodiments, administration of an ISS-containing polynucleotide results in a reduction in viral titer (a reduction of which indicates suppression of viral infection). In some embodiments, duration of respiratory viral infection is reduced. In other embodiments, viral infection is suppressed, which may be indicated by any one or more of a number of parameters, including, but not limited to, extent of one or more symptoms and viral titer.

Symptoms of infection may be assessed before and/or after administration of ISS-containing polynucleotide by the individual or the clinician. Rhinitis, nasal mucous production, severity of cough, myalgia, elevated body temperature, and other symptoms of respiratory virus infection may be easily measured using simple tests and/or scales as are known in the art.

Viral titer may be assessed in biological samples using standard methods of the art. Levels of viral nucleic acid may be assessed by isolating nucleic acid from the sample and blot analysis using a viral polynucleotide sequence as a probe, or PCR analysis. Another assay is to test for virus particles in the sample. Another assay is for plaque forming units (PFU). Another assay measures virus induced cytopathic effects (CPE), such as formation of syncytia, as is described in the Examples. Extent or amount of viral particles may be measured from any infected area, such as infected tissue or mucosal discharge. When the sample is a liquid, viral titer is calculated in some indication of number or amount of virus or virus particles (e.g., infectious particles, plaque forming units, infectious doses, or median tissue culture infectious doses (TCID 50)) per unit volume. In solid samples, such as a tissue sample, viral titer is calculated in virus particles per unit weight. Reduction is indicated by comparing an estimated titer (based, for example, on animal or clinical studies)

that represents untreated infection, and/or a titer measured at an earlier timepoint, with the measured viral titer after treatment.

Kits of the Invention

The invention provides kits for carrying out the methods of the invention. Accordingly, a variety of kits are provided. The kits may be used for any one or more of the following (and, accordingly, may contain instructions for any one or more of the following uses): reducing severity of a symptom of a respiratory virus infection in an individual at risk of being exposed to, exposed to or infected by a respiratory virus; suppressing infection in an individual at risk of being exposed to, exposed to or infected by a respiratory virus; preventing a symptom of a respiratory virus infection in an individual at risk of being exposed to, exposed to or infected by a respiratory virus; delaying development of a symptom of a respiratory virus infection in an individual at risk of being exposed to, exposed to or infected by a respiratory virus; reducing duration of a respiratory virus infection in an individual at risk of being exposed to, exposed to or infected by a respiratory virus. As is understood in the art, any one or more of these uses would be included in instructions directed to treating or preventing a respiratory virus infection.

The kits of the invention comprise one or more containers comprising an ISS-containing polynucleotide and a set of instructions, generally written instructions although electronic storage media (e.g., magnetic diskette or optical disk) containing instructions are also acceptable, relating to the use and dosage of the ISS-containing polynucleotide for the intended treatment (e.g., reducing severity of a symptoms of a respiratory virus infection in an individual at risk of being exposed to, exposed to, or infected by a respiratory virus, suppressing infection in an individual at risk of being exposed to, exposed to, or infected by a respiratory virus, preventing a symptom of a respiratory virus infection in an individual at risk of being exposed to, exposed to, or infected by a respiratory virus, delaying development of a symptom of a respiratory virus infection in an individual at risk of being exposed to, exposed to, or infected by a respiratory virus, and/or reducing duration of a respiratory virus infection in an individual at risk of being exposed to, exposed to, or infected by a respiratory virus). The instructions included with the kit generally include information as to dosage, dosing schedule, and route of administration for the intended treatment. The containers of ISS-containing polynucleotide may be unit doses, bulk packages (e.g., multi-dose vials) or sub-unit doses.

The kits of the invention do not include any packages or containers which contain viral antigens from the respiratory virus(es) the kit is intended to be used to treat. For example, in a kit intended for the prevention, suppression, amelioration or treatment of RSV, neither the container(s) comprising the ISS-containing polynucleotide nor any other containers in the kit contain viral antigens from the RSV.

The ISS-containing polynucleotide component of the kit may be packaged in any convenient, appropriate packaging. For example, if the ISS is a freeze-dried formulation, a vial with a resilient stopper is normally used, so that the drug may be easily reconstituted by injecting fluid through the resilient stopper. Ampoules with non-resilient, removable closures (e.g., sealed glass) or with resilient stoppers are most conveniently used for injectable forms of ISS. Also, prefilled syringes may be used when the kit is supplied with a liquid formulation of the ISS-containing polynucleotide. The kit may contain the ISS in an ointment for topical formulation in appropriate packaging. Also contemplated are packages for use in combination with a specific device, such as an inhaler, nasal administration device (e.g., an atomizer) or an infusion device such as a minipump or transdermal administration device.

As stated above, any ISS-containing polynucleotide described herein may be used, such as, for example, any polynucleotide comprising any of the following ISS: the sequence 5'-cytosine, guanine-3', the sequence 5'-T, C, G-3', the sequence 5'-C, G, pyrimidine, pyrimidine, C, G-3', the sequence 5'-purine, purine, C, G, pyrimidine, pyrimidine, C, G-3', the sequence 5'-purine, purine, C, G, pyrimidine, pyrimidine, C, C-3'; the sequence SEQ ID NO: 1018; the sequence 5'-purine, purine, B, G, pyrimidine, pyrimidine-3' wherein B is 5-bromocytosine or the sequence 5'-purine, purine, B, G, pyrimidine, pyrimidine, C, G-3' wherein B is 5-bromocytosine.

The following Examples are provided to illustrate, but not limit, the invention.

EXAMPLES

Example 1

Animal Model and Experimental Methods for Respiratory Viruses

Rat Model for RSV Infection and ISS Administration

Cotton rats, 50-100 g and 4-12 weeks old (*Sigmoden hispidis*) of either sex were used in these studies. All of the animals were descendants of two pair of cotton rats obtained in 1984 from the Small Animal Section of the Veterinary Research Branch, Division of Research Services, National Institutes of Health.

RSV strain A2 was purchased from the ATCC (ATCC VR26). Working stocks of this virus were prepared as described in detail by Wyde et al. (1995) *Pediatr. Res.* 238: 543-550. ISS sequence tested for RSV experiments was 5'-TGACTGTGAACGTTCGAGATGA-3' (SEQ ID NO:1) (phosphorothioate). Control, non-ISS sequences used were 5'-TGACTGTGAAGGTTAGAGATGA-3' (SEQ ID NO:9) (phosphorothioate) and 5'-TCACTCTCTTCCTTACTCT-TCT-3' (SEQ ID NO:10) (phosphorothioate), as well as PBS.

Assay for RSV Viral Titer

RSV levels in virus pools and lung lavage fluids (L.F.) were determined using sterile 96-well, flat bottom tissue culture plates (Falcon 3072), serial 3-fold dilutions and 2% FCS-MEM as described in detail previously (Wyde et al., 1995). The wells in these assay plates were observed for virus-induced cytopathic effects (CPE) including formation of synctia. After the dilutions in the last wells of replicate rows exhibiting virus-induced CPE were determined, mean virus titers were calculated using the method of Karber, Rhodes and Van Rhodes and Van Rooyen (1953) *Textbook of Virology* (2nd ed. Williams and Wilkins pp 66-69). The amount of virus in virus pools was expressed as a median tissue culture infectious doses ($TCID_{50}$/ml, logo). Titers of virus in L.F. were expressed as $TCID_{50}$/g lung tissue ($log_{10}$). The minimum detectable virus concentration in these assays was 1.3 $log_{10}$ $TCID_5O$/ml (virus pools) or 1.6 $log_{10}$ $TCID_{50}$/g lung.

Example 2

Local Administration of ISS Reduces RSV Viral Titer

These experiments were performed to test the effect of local administration of ISS in terms of antiviral activity against respiratory syncytial virus (RSV) in cotton rats.

On day −3 (i.e., 3 days before infection with virus), 20 cotton rats (CRs) were selected and divided into five groups of four animals. The animals in Group 1 were lightly anesthetized and 50 μL of phosphate buffered saline (PBS) was administered intranasally (IN). The CRs in Group 2 were similarly administered 150 μg of ISS (5'-TGACTGT-GAACGTTCGAGATGA-3') (SEQ ID NO:1), while the animals in Group 3 were similarly administered 150 μg of control non-ISS sequence 5'-TGACTGTGAAGGTTAGAGATGA-3' (SEQ ID NO:9). Three days later, on Day 0, each of CRs in Group 4 were anesthetized and 150 μg of ISS was administered 1N, and the animals in Group 5 were administered, in a like manner, 150 μg of control non-ISS sequence 5'-TGACTGTGAAGGTTA-GAGATGA-3' (SEQ ID NO:9).

Thirty minutes later, all of the CRs were inoculated IN with 100 median tissue culture infectious doses ($TCID_{50}$) of RSV A2. Four days later (Day 4), all of the animals were sacrificed and the lungs of each animal were removed, lavaged, and assessed for RSV levels. A summary of the protocol is shown in Table 1. The results are shown in FIG. 1 and Table 2.

TABLE 1

| | | Protocol | | | |
|---|---|---|---|---|---|
| Group | ISS admin. | Dose ISS given (μg/CR) | Day ISS given | Day RSV given | Day CRs harvested | End-point |
| 1 | PBS | 0 | Day −3 | Day 0 | Day 4 | RSV in lung |
| 2 | ISS | 150 | Day −3 | Day 0 | Day 4 | RSV in lung |
| 3 | non-ISS | 150 | Day −3 | Day 0 | Day 4 | RSV in lung |
| 4 | ISS | 150 | Day 0 | Day 0 | Day 4 | RSV in lung |
| 5 | non-ISS | 150 | Day 0 | Day 0 | Day 4 | RSV in lung |

TABLE 2

| | | | RSV Titers | | | | |
|---|---|---|---|---|---|---|---|
| | | Day | RSV titer ($log_{10}$/g lung) in CR No. | | | | Std. |
| Group | Treatment | given | 1 | 2 | 3 | 4 | Mean | Dev. |
| 1 | PBS | −3 | 4.5 | 4.5 | 3.5 | 4 | 4.1 | 0.5 |
| 2 | ISS | −3 | 3 | 3 | 2.5 | 2.5 | 2.8 | 0.3 |
| 3 | non-ISS | −3 | 4.5 | 4.5 | 3.5 | 4 | 4.1 | 0.5 |
| 4 | ISS | 0 | 4 | 4 | 4.5 | 3 | 3.9 | 0.6 |
| 5 | non-ISS | 0 | 4.5 | 4 | 4.5 | 3 | 4.0 | 0.7 |

Using the Kruskall-Wallis nonparametric ANOVA p = 0.061, not quite statistically significant.

These results indicate that administration of ISS reduced viral titer in infected tissue compared to PBS or non-ISS administration. The results also indicate that a first administration of ISS on the day of infection was not effective, while administration before infection (in this experiment, 3 days) was effective at reducing viral titers.

Example 3

Non-Local Administration of ISS and RSV Viral Titer

These experiments were performed to test the effect of non-local administration of ISS in terms of antiviral activity against RSV in cotton rats.

Twenty cotton rats were divided into 5 groups of 4 animals. Administered to these animals, either intraperitoneally (IP) or subcutaneously (SC), was PBS, immunostimulatory sequence (ISS) 5'-TGACTGTGAACGTTCGAGATGA-3' (SEQ D NO:1) or non-ISS sequence 5'-TCACTCTCTTCCT-TACTCTTCT-3' (SEQ ID NO:10), each sequence at 150 μg/injection. On Day 0 each of these animals was inoculated IN with 100 $TCID_{50}$ of RSV A2. Four days later each cotton rat was sacrificed. The lungs of each animal were removed, lavaged and assessed for RSV. The protocol is summarized in Table 3. The results from IP administration are shown in Table 4. The results from SC administration are shown in Table 5.

TABLE 3

| | | Protocol | | | |
|---|---|---|---|---|---|
| Group | ISS admin. | Dose ISS given (μg/CR) | Day ISS given | Day RSV given | Day CRs Sacrificed | End-point |
| 1 | PBS | 0 | −3, −1 | 0 | Day 4 | RSV in lung |
| 2 | ISS | 150 | −1 | 0 | Day 4 | RSV in lung |
| 3 | ISS | 150 | −3 | 0 | Day 4 | RSV in lung |
| 4 | non-ISS | 150 | −1 | 0 | Day 4 | RSV in lung |
| 5 | non-ISS | 150 | −3 | 0 | Day 4 | RSV in lung |

TABLE 4

| | | RSV Titers | | | | | | |
|---|---|---|---|---|---|---|---|---|
| | Treatment | Day(s) | RSV titer ($log_{10}$/g lung) in cotton rat no. | | | | | Std. |
| Group | (IP) | given | 1 | 2 | 3 | 4 | Mean | Dev. |
| 1 | PBS | −1, −3 | 4.3 | 3.8 | 3.8 | 3.3 | 3.8 | 0.3 |
| 2 | ISS | −1 | 3.8 | 3.3 | 3.3 | 3.8 | 3.6 | 0.3 |
| 3 | ISS | −3 | 3.3 | 3.8 | 3.8 | 3.8 | 3.7 | 0.3 |
| 4 | Non-ISS | −1 | 1.8 | 3.3 | 3.8 | 3.3 | 3.1 | 0.9 |
| 5 | Non-ISS | −3 | 3.3 | 4.3 | 3.3 | 3.3 | 3.6 | 0.5 |

TABLE 5

| | | RSV titers | | | | | | |
|---|---|---|---|---|---|---|---|---|
| | Treatment | Days | RSV titer ($log_{10}$/g lung) in CR no. | | | | | Std. |
| Group | (SC) | given | 1 | 2 | 3 | 4 | Mean | Dev. |
| 1 | PBS | −1, −3 | 4 | 4 | 3.5 | 4 | 3.9 | 0.3 |
| 2 | ISS | −1 | 4 | 4.5 | 3.5 | 4 | 4.0 | 0.4 |
| 3 | ISS | −3 | 4 | 4.5 | 4 | 4 | 4.1 | 0.3 |
| 4 | Non-ISS | −1 | 4.5 | 4.5 | 3.5 | 4 | 4.1 | 0.5 |
| 5 | Non-ISS | −3 | 3.5 | 4 | 4 | 3.5 | 3.8 | 0.3 |

In each experiment, IP and SC administration of 150 μg of ISS-containing polynucleotide failed to cause a statistically significant reduction in viral titers compared to PBS administration.

Example 4

Local Administration of ISS and Influenza Viral Titer

These experiments were performed to test the effect of local administration of ISS in terms of antiviral activity against influenza virus in mice.

Thirty-five mice were divided into 5 groups of 7 animals each. On Day −3 (relative to virus inoculation), PBS (50 μl) was administered intranasally (IN) to the animals in Group 1, while ISS 5'-TGACTGTGAACGTTCGAGATGA-3' (SEQ ID NO:1) was administered IN (50 μg in 50 μl/mouse) to the animals in Group 2 and non-ISS control sequence 5'-TGACT-GTGAAGGTTAGAGATGA-3' (SEQ ID NO:9) was administered IN (50 μg in 50 μl/mouse) to the animals in Group 3. Three days later (Day 0), ISS (50 μg/mouse) or non-ISS control of sequence (50 μg/mouse) were administered IN to the animals in Groups 4 and 5, respectively. On day 0, 50 μL of PBS was administered IN to the animals in Group 1. Shortly after these administrations on day 0, all of the mice were inoculated IN with approximately 100 median tissue culture infectious doses ($TCID_{50}$) of influenza A/Mississippi (H3N2) virus. Four days later, all of the mice were sacrificed and the lungs of each were tested for influenza virus titer. The protocol is summarized in Table 6. The results are summarized in Table 7. The results show that IN administration of this dose of ISS before viral infection fails to cause a satisfactory significant reduction in virus titer compared to PBS administration.

TABLE 6

Protocol

| Group | Treatment | Day given | Virus inoc. | Day Sacrifice | Test parameter |
|---|---|---|---|---|---|
| 1 | PBS | −3, 0 | Day 0 | Day 4 | Pulmonary |
| 2 | ISS | −3 | Day 0 | Day 4 | virus |
| 3 | non-ISS | −3 | Day 0 | Day 4 | titer |
| 4 | ISS | 0 | Day 0 | Day 4 | |
| 5 | non-ISS | 0 | Day 0 | Day 4 | |

TABLE 7

Influenza Virus Titers

| Group | Treatment | Day ISS given | Pulmonary virus titer ($log_{10}$/lung) in mouse no. 1 | 2 | 3 | 4 | 5 | 6 | 7 | Mean | Std. Dev. |
|---|---|---|---|---|---|---|---|---|---|---|---|
| 1 | PBS | −3, 0 | 3.5 | 4 | 4.5 | 6 | 4.5 | 4.5 | 4 | 4.4 | 0.8 |
| 2 | ISS | −3 | 5.5 | 4 | 6 | 5.5 | 5 | 4 | 3 | 4.7 | 1.1 |
| 3 | non-ISS | −3 | 3.5 | 3.5 | 4 | 3 | 5 | 5 | 4 | 4.0 | 0.8 |
| 4 | ISS | 0 | 4 | 5.5 | 5 | 4.5 | 4.5 | 4.5 | 4.5 | 4.6 | 0.5 |
| 5 | non-ISS | 0 | 5.5 | 4 | 4.5 | 4.5 | 6 | 5.5 | 4.5 | 4.9 | 0.7 |

Example 5

Non-Local Administration of ISS and Influenza Viral Titer

These experiments were performed to test the effect of non-local administration of ISS in terms of antiviral activity against influenza virus in mice.

Twenty-five mice were divided into 5 groups of 5 animals each. On Day −3 (relative to virus inoculation), PBS was administered intraperitoneally (IP) to the animals in Group 1, while ISS 5'-TGACTGTGAACGTTCGAGATGA-3' (SEQ ID NO:1) was administered IP (50 μg/mouse) to the animals in Group 3 and non-ISS control sequence 5'-TCACTCTCT-TCCTTACTCTTCT-3' (SEQ ID NO:10) was administered IP (50 μg/mouse) to the animals in Group 5. On Day −1, ISS (50 μg/mouse) or non-ISS control of sequence (50 μg/mouse) were administered IP to the animals in Groups 2 and 4, respectively. The next day (Day 0), all of the mice were inoculated intranasally (IN) with approximately 100 median $TCID_{50}$ of influenza A/Mississippi (H3N2) virus. Four days later, all of the mice were sacrificed and the lungs of each were tested for influenza virus titer. The protocol is summarized in Table 8. The results are summarized in Table 9. The results show that IP administration of this dose of ISS before viral infection fails to cause a satisfactory significant reduction in virus titer compared to PBS administration.

TABLE 8

Protocol

| Group | Treatment | Day given | Virus inoc. | Day Sacrifice | Test parameter |
|---|---|---|---|---|---|
| 1 | PBS | −3, −1 | Day 0 | Day 4 | Pulmonary |
| 2 | ISS | −1 | Day 0 | Day 4 | virus |
| 3 | ISS | −3 | Day 0 | Day 4 | titer |
| 4 | non-ISS | −1 | Day 0 | Day 4 | |
| 5 | non-ISS | −3 | Day 0 | Day 4 | |

TABLE 9

Influenza Virus Titers

| Group | Treatment | Day ISS given | Pulmonary virus titer ($log_{10}$/lung) in mouse no. 1 | 2 | 3 | 4 | 5 | Mean | Std. Dev. |
|---|---|---|---|---|---|---|---|---|---|
| 1 | None | −3, −1 | 5.8 | 7.3 | 5.8 | 6.3 | 6.3 | 6.3 | 0.6 |
| 2 | ISS | −1 | 6.3 | 6.8 | 7.3 | 6.8 | 6.8 | 6.8 | 0.4 |
| 3 | ISS | −3 | 7.3 | 5.8 | 7.3 | 6.8 | 7.3 | 6.9 | 0.7 |
| 4 | non-ISS | −1 | 6.8 | 6.3 | 5.8 | 5.8 | 5.8 | 6.1 | 0.4 |
| 5 | non-ISS | −3 | 5.8 | 5.8 | 6.3 | 7.3 | 7.3 | 6.5 | 0.8 |

The present invention has been detailed both by direct description and by example. Equivalents and modifications of the present invention will be apparent to those skilled in the art, and are encompassed within the scope of the invention.

What is claimed is:

1. A method of suppressing a respiratory syncytial virus (RSV) infection in an individual who is at risk of being exposed to RSV, comprising administering a composition locally to the respiratory tract of said individual, said composition comprising a polynucleotide comprising an immunostimulatory sequence (ISS), wherein the ISS comprises the sequence 5'-CGTTCG-3', wherein the polynucleotide is greater than 6 and less than about 100 nucleotides in length, wherein RSV antigen, an immunostimulatory cytokine, and an adjuvant are not administered in conjunction with administration of said composition, wherein said individual is a human, wherein said composition is administered prior to exposure to RSV, and wherein said polynucleotide is administered in an amount sufficient to reduce RSV titer.

2. The method of claim 1, wherein the ISS comprises a sequence selected from the group consisting of 5'-AACGTTCG-3' and 5'-GACGTTCG-3'.

3. The method of claim 1, wherein the ISS comprises the sequence 5'-TGACTGTGAACGTTCGAGATGA-3' (SEQ ID NO:1).

4. The method of claim 1, wherein administration is to a lung.

5. The method of claim 1, wherein administration is to nasal passages.

6. The method of claim 1, wherein the polynucleotide comprises a phosphate backbone modification.

7. The method of claim 1 wherein said composition further comprises a pharmaceutically-acceptable excipient.

* * * * *

SEQUENCE LISTING

<160> NUMBER OF SEQ ID NOS: 10

<210> SEQ ID NO 1
<211> LENGTH: 22
<212> TYPE: DNA
<213> ORGANISM: Artificial Sequence
<220> FEATURE:
<223> OTHER INFORMATION: Polynucleotide containing CG

<400> SEQUENCE: 1
tgactgtgaa cgttcgagat ga                                              22

<210> SEQ ID NO 2
<211> LENGTH: 22
<212> TYPE: DNA
<213> ORGANISM: Artificial Sequence
<220> FEATURE:
<223> OTHER INFORMATION: Polynucleotide containing CG

<400> SEQUENCE: 2
tgaccgtgaa cgttcgagat ga                                              22

<210> SEQ ID NO 3
<211> LENGTH: 23
<212> TYPE: DNA
<213> ORGANISM: Artificial Sequence
<220> FEATURE:
<223> OTHER INFORMATION: Polynucleotide containing CG

<400> SEQUENCE: 3
tcatctcgaa cgttccacag tca                                             23

<210> SEQ ID NO 4
<211> LENGTH: 22
<212> TYPE: DNA
<213> ORGANISM: Artificial Sequence
<220> FEATURE:
<223> OTHER INFORMATION: Polynucleotide containing CG

<400> SEQUENCE: 4
tgactgtgaa cgttccagat ga                                              22

<210> SEQ ID NO 5
<211> LENGTH: 26
<212> TYPE: DNA
<213> ORGANISM: Artificial Sequence
<220> FEATURE:
<223> OTHER INFORMATION: Polynucleotide containing CG

<400> SEQUENCE: 5
tccataacgt tcgcctaacg ttcgtc                                          26

<210> SEQ ID NO 6
<211> LENGTH: 22
<212> TYPE: DNA
<213> ORGANISM: Artificial Sequence
<220> FEATURE:
<223> OTHER INFORMATION: Polynucleotide containing (5-bromocytosine) G
<220> FEATURE:
<221> NAME/KEY: misc_feature
<222> LOCATION: 11
<223> OTHER INFORMATION: n = 5-bromocytosine

<400> SEQUENCE: 6
tgactgtgaa ngttccagat ga                                              22

<210> SEQ ID NO 7
<211> LENGTH: 22
<212> TYPE: DNA
<213> ORGANISM: Artificial Sequence
<220> FEATURE:
<223> OTHER INFORMATION: Polynucleotide containing (5-bromocytosine) G
<220> FEATURE:
<221> NAME/KEY: misc_feature
<222> LOCATION: 11
<223> OTHER INFORMATION: n = 5-bromocytosine

<400> SEQUENCE: 7

```
tgactgtgaa ngttcgagat ga                                              22

<210> SEQ ID NO 8
<211> LENGTH: 22
<212> TYPE: DNA
<213> ORGANISM: Artificial Sequence
<220> FEATURE:
<223> OTHER INFORMATION: Polynucleotide containing (5-bromocytosine) G
<220> FEATURE:
<221> NAME/KEY: misc_feature
<222> LOCATION: 11, 15
<223> OTHER INFORMATION: n = 5-bromocytosine

<400> SEQUENCE: 8
tgactgtgaa ngttngagat ga                                              22

<210> SEQ ID NO 9
<211> LENGTH: 22
<212> TYPE: DNA
<213> ORGANISM: Artificial Sequence
<220> FEATURE:
<223> OTHER INFORMATION: Polynucleotide not containing CG

<400> SEQUENCE: 9
tgactgtgaa ggttagagat ga                                              22

<210> SEQ ID NO 10
<211> LENGTH: 22
<212> TYPE: DNA
<213> ORGANISM: Artificial Sequence
<220> FEATURE:
<223> OTHER INFORMATION: Polynucleotide not containing CG

<400> SEQUENCE: 10
tcactctctt ccttactctt ct                                              22
```